(12) United States Patent
Ishikawa et al.

(10) Patent No.: US 7,080,543 B2
(45) Date of Patent: Jul. 25, 2006

(54) SENSOR AND METHOD FOR MANUFACTURING THE SAME

(75) Inventors: Hideki Ishikawa, Aichi (JP); Yoshikuni Sato, Aichi (JP); Keigo Banno, Aichi (JP); Masashi Sakamoto, Aichi (JP); Noboru Ishida, Gifu (JP); Takafumi Oshima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/409,587

(22) Filed: Apr. 9, 2003

(65) Prior Publication Data
US 2004/0003664 A1  Jan. 8, 2004

(30) Foreign Application Priority Data
Apr. 10, 2002 (JP) ............................. 2002-107459

(51) Int. Cl.
*G01N 29/02* (2006.01)
(52) U.S. Cl. .................. 73/24.06; 73/632; 310/336
(58) Field of Classification Search ............... 73/24.06, 73/597, 632, 644; 310/334, 336
See application file for complete search history.

(56) References Cited

U.S. PATENT DOCUMENTS

| | | | |
|---|---|---|---|
| 3,890,423 A * | 6/1975 | Zacharias, Jr. ............... | 73/644 |
| 4,365,515 A * | 12/1982 | Abts ........................... | 73/632 |
| 4,773,267 A * | 9/1988 | Abts ........................... | 73/597 |
| 5,627,323 A | 5/1997 | Stern | |
| 5,814,736 A * | 9/1998 | Loschberger et al. .... | 73/861.25 |
| 6,268,683 B1 * | 7/2001 | Li ............................... | 310/334 |

FOREIGN PATENT DOCUMENTS

| | | |
|---|---|---|
| EP | 0 661 536 A1 | 7/1995 |
| JP | 1-70158 | 5/1989 |
| JP | 8-5615 | 1/1996 |
| JP | 8-94590 | 4/1996 |
| JP | 2002-31621 | 1/2002 |

OTHER PUBLICATIONS

Myrna C. Sultan et al.., "Closed Loop Canister Purge Control System", SAE Technical Paper Series No. 980206, International Congress and Exposition, Detroit, Michigan, Feb. 23-26, 1998, 8 pages.
M. Habaguchi et al., "Gasoline Vapor Concentration Sensor—On Board Measurement by Ultrasonic Pulse-", Proceedings for Society of Automotive Engineers of Japan 955, Sep. 1995, pp. 89-92.

* cited by examiner

*Primary Examiner*—John E. Chapman
(74) *Attorney, Agent, or Firm*—Sughrue Mion, PLLC

(57) ABSTRACT

A detecting-element assembly (40) is configured such that a piezoelectric element (51) is housed in a casing body portion (43) of a casing (42), and is attached to a housing portion (22) of a flow path formation member (20) via a flange portion (41). Therefore, the path between the piezoelectric element (51) and the position of attachment of the detecting-element assembly (40) is elongated, whereby ultrasonic waves which leak into the interior of the detecting-element assembly (40) from the piezoelectric element (51) become unlikely to reflectively return from a joint. Thus, the influence of, for example, noise stemming from reflected waves is reduced, thereby enhancing the accuracy of detection. An average clearance of 1 millimeter or more is provided along the outer circumferential surface of the casing body portion (43) of the detecting-element assembly (40), whereby a problem of collected foreign matter is unlikely to occur.

13 Claims, 14 Drawing Sheets

SENSOR AND METHOD FOR MANUFACTURING THE SAME

BACKGROUND OF THE INVENTION

1. Field of the Invention

The present invention relates to a sensor configured such that an element casing, housing an element for transmitting and receiving ultrasonic waves and electric signals, is attached to a measuring chamber in which an object to be measured by use of ultrasonic waves is present, as well as to a method for manufacturing the sensor.

2. Description of the Related Art

Conventionally, an assembly of an element for transmitting and receiving ultrasonic waves and electric signals and a casing housing the element has been used as a sensor or an ultrasonic-wave generator. Ultrasonic waves propagate through various media. Since the propagation of ultrasonic waves is influenced by properties of a medium, such as concentration, thickness, and temperature, ultrasonic waves are utilized for sensing such properties. For example, in a known gas sensor, an ultrasonic-wave generator that faces a flow path is used for measuring the concentration, temperature, or humidity of a gas present in the flow path. Such a gas sensor electrically processes a signal emitted from a detecting element and outputs an electric signal corresponding to a property of the gas. Examples of such a gas sensor include a gas concentration sensor used in transportation equipment on which an internal combustion engine is mounted, such as an automobile, for detecting the concentration of gasoline or light oil through utilization of variation in propagation speed of ultrasonic waves. Such a gas concentration sensor is disposed in, for example, a purge line extending between a canister mounted on an automobile and an intake pipe of an internal combustion engine of the automobile, and is configured such that an evaporated fuel gas which contains gasoline flows through a flow path of a predetermined volume formed therein. As the concentration of gasoline vapor varies, the speed of ultrasonic waves propagating through the medium varies. An ultrasonic receiver detects this variation of speed and conducts signal processing so as to output a signal corresponding to the gasoline concentration. Usually, the time required for an ultrasonic wave transmitted from a transmitter to propagate over a predetermined distance and reach a receiver is measured, and the gasoline concentration is obtained from the measured time.

Most detecting elements including that of such a gas concentration sensor cannot directly convert variation in a property of a gas to an intensive electric signal; i.e., electric signals output from these detecting elements are weak. Therefore, in a conventional gas sensor, an electric signal emitted from a detecting element is amplified and processed by means of a dedicated signal processing circuit.

Although weakness of an electric signal is solved through amplification and processing, enhancing detection accuracy has been difficult if noise is superposed on a signal which an element is to detect. Conventional sensors have failed to sufficiently reduce the influence of ultrasonic noise on a detecting action of an element, regardless of whether the sensors employ a single element which serves as a transmitter-receiver for transmission and reception of ultrasonic waves, or a transmitter element and a receiver element that are provided separately. Usually, an element casing that houses an element is formed separately from a measuring chamber in which an object to be measured, such as gas, is present. In some cases, attachment of this gas sensor to a measuring chamber in a fixed condition has involved a phenomenon such that ultrasonic waves propagate through an outer wall which defines the measuring chamber, and reach the detecting element. Some cases where an element for transmitting ultrasonic waves is housed in a sensor have involved a phenomenon such that ultrasonic waves transmitted from the element are reflected from a joint between the sensor and a measuring chamber, and the thus-reflected waves are received by a receiving element and act as noise in measurement.

SUMMARY OF THE INVENTION

An object of the present invention is to solve the above-mentioned problems and to provide a sensor which is unlikely to pick up noise stemming from detouring or reflection of ultrasonic waves.

A sensor of the present invention which solves at least a portion of the above-described problem comprises an element for transmitting and receiving ultrasonic waves and electric signals, an element casing housing the element, and a measuring chamber, the element casing being attached to the measuring chamber, and an object to be measured by use of ultrasonic waves being present in the measuring chamber, wherein the element casing comprises a body portion for housing the element and a flange portion to be attached to the measuring chamber;

the element is attached to a first end of the body portion; and the flange portion is integrated with a second end of the body portion located in opposition to the first end, to which the element housed in the body portion is attached.

This sensor is configured such that the element casing is attached to the measuring chamber via the flange portion thereof. The element housed in the element casing is attached to the first end of the body portion, and the flange portion is integrated with the second end of the body portion located in opposition to the first end, to which the element housed in the body portion is attached. Therefore, as viewed from the element for transmitting and receiving ultrasonic waves and electric signals, the far side of the element casing is fixedly attached to the measuring chamber; thus, the element is not susceptible to the influence of ultrasonic waves reflected from the fixation portion or detouring ultrasonic waves on the side where measurement is performed.

Further optional features of preferred embodiments of the invention are as follows.

The body portion of the element casing can be molded from a synthetic resin. In this case, the flange portion can be readily formed integrally with the body portion.

Furthermore, the element casing can be configured such that the body portion is tubular and such that the first end of the body portion is sealed with a sealing member. In this case, the element may be bonded to the sealing member directly or via a member that aids transmission of ultrasonic waves. The tubular body portion can be filled with resin while housing the element. This configuration facilitates transmission and reception of ultrasonic waves between the sensor and an external element, and can enhance reliability of the element casing.

A portion of the measuring chamber to which the element casing is attached can be one of inner walls which define the measuring chamber. The inside diameter of the portion of the measuring chamber to which the element casing is attached is made greater than the outside diameter of the element casing. Preferably, the inside diameter is 2 mm or more greater than the outside diameter. A diametral difference of 2 mm or more provides an average clearance of 1 mm, whereby ultrasonic reverberations in the element are reduced, and foreign matter or the like is unlikely to be collected in the clearance.

In this sensor, no particular limitation is imposed on an object to be measured, or on a medium such as gas or liquid. For example, this sensor can be configured as a gas concentration sensor such that the object to be measured is a gas and in such a manner as to comprise a detecting portion for detecting the condition of transmission of ultrasonic waves by means of an electric signal received from the element and determining the concentration of the gas from the detected condition. Assuming a simple structure, this gas sensor can accurately measure the concentration of gas in a non-contacting manner.

When ultrasonic waves are to be used, an ultrasonic transmitter and an ultrasonic receiver may be provided separately. However, a single element can serve as an ultrasonic transmitter-receiver. For example, the sensor can be configured such that the element casing is provided at a first end of the measuring chamber in which an object to be measured is present, and a reflective portion for reflecting ultrasonic waves is provided at a second end of the measuring chamber, and such that ultrasonic waves which are transmitted from the element casing and then reflected from the reflective portion are received by the same element housed in the element casing. In this case, by measuring time between transmission of an ultrasonic wave from the element casing and reception of the ultrasonic wave reflected from the reflective portion, the concentration of gas can be determined from the measured time. Use of a transmitter-receiver element simplifies the overall configuration of the sensor.

The flange portion and the body portion can be embodied in various relational forms. For example, the outside diameter of the flange portion is greater than that of the body portion. Alternatively, the flange portion comprises a portion having an outside diameter smaller than that of the body portion and integrated with a central part of the second end of the body portion. In either case, preferably, the flange portion is fixedly attached to the measuring chamber at a position located distantly from the element, in order to enhance noise resistance.

A second aspect of the present invention provides a sensor comprising an element for transmitting and receiving ultrasonic waves and electric signals, an element casing housing the element, and a measuring chamber, the element casing being provided in the measuring chamber, and an object to be measured by use of ultrasonic waves being present in the measuring chamber, wherein the element casing comprises a tubular portion for housing the element, the tubular portion and the measuring chamber being integrally formed from resin;

the tubular portion is integrated with the measuring chamber at a position located a predetermined distance away from a region of the measuring chamber in which the object is present;

the element is housed in the tubular portion of the element casing at an end of the tubular portion located on a side toward the measuring chamber; and the end of the tubular portion located on the side toward the measuring chamber is sealed.

In contrast to the sensor of the first aspect of the invention, this sensor is configured such that the element casing is not formed as a separate member, but includes the tubular portion which houses the element and is formed from resin integrally with the measuring chamber. The tubular portion is integrated with the measuring chamber at a position located a predetermined distance away from a region of the measuring chamber in which the object is present. Also, the element is housed in the tubular portion at an end thereof located on the side toward the measuring chamber, and the end of the tubular portion is sealed. Therefore, as in the case of the first invention, the element for transmitting and receiving ultrasonic waves and electric signals and the tubular portion housing the element are joined together at a position located away from the measuring chamber, whereby the element is not susceptible to the influence of reflected ultrasonic waves and detouring ultrasonic waves.

The present invention further provides a method for manufacturing a sensor comprising an element for transmitting and receiving ultrasonic waves and electric signals, an element casing housing the element, and a measuring chamber, an object to be measured by use of ultrasonic waves being present in the measuring chamber, the method comprising the steps of:

forming the element casing from resin in such a manner as to comprise a body portion for housing the element, and a flange portion integrated with the body portion;

housing the element in the body portion at an end of the body portion and then substantially filling the interior of the body portion with resin; and fixing the element casing in such an orientation that the body portion is located within the measuring chamber and such that the flange portion comes into contact with a fixation portion of the measuring chamber from the outside of the measuring chamber.

This method for manufacturing a sensor allows the flange portion to be readily attached to the measuring chamber in a fixed condition while the element casing which houses the element faces the measuring chamber.

Figure 1:
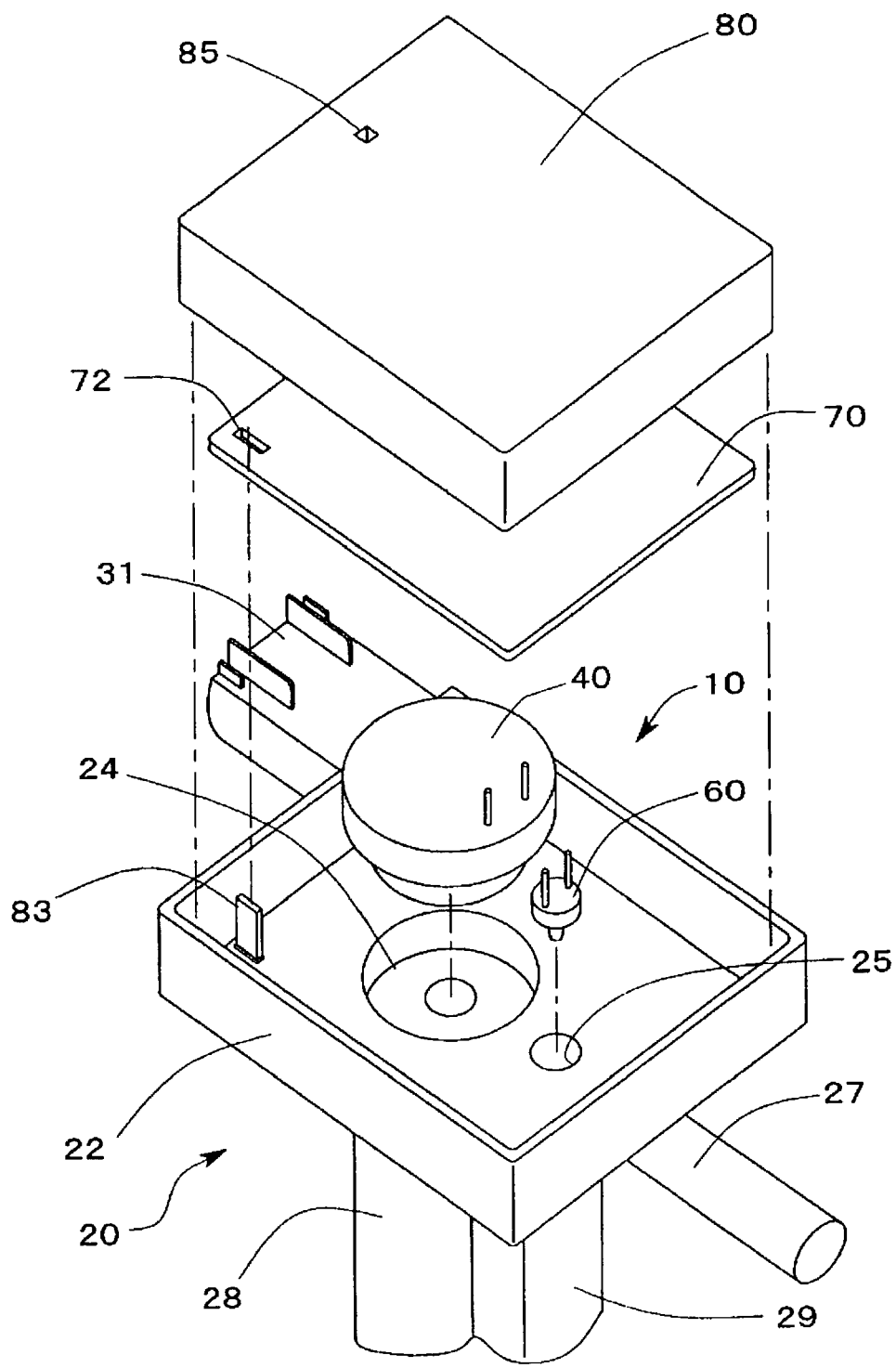
FIG. 1 is an exploded perspective view showing a schematic configuration of a gas sensor 10 according to an embodiment of the present invention.

Reference numerals are used to identify items shown in the drawings as follows:

10 . . . gas sensor
20 . . . flow path formation member
22 . . . housing portion
24 . . . recess
25 . . . mounting hole
27 . . . introduction path
28 . . . measuring chamber
29 . . . bypass
31 . . . connector
32 . . . inlet hole
33 . . . reflective portion
34 . . . outlet
35 . . . discharge path
36 . . . metal plate
40, 400 . . . detecting-element assembly
41 . . . flange portion
42 . . . element casing
43 . . . casing body portion
45 . . . end face
46 . . . stepped portion
48 . . . film
49 . . . support
50 . . . acoustic matching plate
51 . . . piezoelectric element
52 . . . tubular member
52*a* . . . polyethylene terephthalate film
52*b* . . . bonding layer
52*c* . . . copper foil
53 . . . opening
54*a*,54*b* . . . lead wires
55*a*,55*b* . . . terminals
56*a*,56*b* . . . protrusions
59 . . . protrusion
60 . . . thermistor
70 . . . electronic circuit board
72 . . . connection hole
80 . . . casing
83 . . . cut-and-raised portion
85 . . . connection hole
88 . . . cushioning material
100 . . . gas sensor
200A . . . upper flow path member
200B . . . lower flow path member
420 . . . container portion

DETAILED DESCRIPTION OF THE PREFERRED EMBODIMENTS

Modes for carrying out the present invention will next be described by way of embodiments and by reference to the drawings. However, the present invention should not be construed as being limited thereto. FIG. 1 is an exploded perspective view of a gas sensor according to an embodiment of the present invention. This gas sensor 10 determines the concentration of gasoline vapor through utilization of a phenomenon in which the propagation speed of ultrasonic waves varies with gas concentration. This gas sensor is disposed in, for example, a path for purging gasoline to an intake path from a canister mounted on a vehicle powered by an internal combustion engine, and is used to determine the concentration of gasoline to be purged.

(A) Overall Configuration of Gas Sensor 10:

As shown in FIG. 1, the gas sensor 10 includes a flow path formation member 20 which forms a flow path through which gas whose concentration is to be determined flows; a detecting-element assembly 40 housed in a housing portion 22 formed integrally with the flow path formation member 20; a thermistor 60 for detecting the temperature of gas flowing through the flow path; an electronic circuit board 70 disposed above the detecting-element assembly 40; and a metal casing 80 fitted in the housing portion 22. The detecting-element assembly 40 is fixedly fitted in a mounting recess 24 formed on the housing portion 22, through ultrasonic welding. The thermistor 60 is fixedly inserted in a mounting hole 25. As will be described later, the detecting-element assembly 40 and the thermistor 60 have terminals for transmitting and receiving electric signals. These terminals are inserted into corresponding connection holes formed in the electronic circuit board 70, followed by soldering. The gas sensor 10 is manufactured in the following manner. After the detecting-element assembly 40 and the thermistor 60 are fixedly attached to the housing portion 22, the electronic circuit board 70 for processing signals is mounted in place. The casing 80 is fitted into the housing portion 22. Then, the thus-formed assembly is molded with resin such as urethane resin. The process for manufacturing the gas sensor 10 will be described later in detail in (G).

(B) Configuration of Flow Path Formation Member 20:

The flow path formation member 20 of the gas sensor 10 is molded from a synthetic resin which contains glass filler. The tensile modulus of the flow path formation member 20 is adjusted so as to be suited for use in a gas sensor. As shown in FIG. 1, the flow path formation member 20 includes the housing portion 22 which is provided at an upper portion thereof so as to house the detecting-element assembly 40, and a flow path which is formed underneath the housing portion 22 and allows the passage of an object gas of measurement. The flow path includes an introduction path 27 for introducing gas containing gasoline vapor into the gas sensor 10; a measuring chamber 28 in which the concentration of gasoline in the gas is detected by means of ultrasonic waves; and a bypass 29 for allowing the gas to bypass the measuring chamber 28. The measuring chamber 28 is located substantially under the detecting-element assembly 40, and the bypass 29 is located substantially under the thermistor 60.

Figure 2:
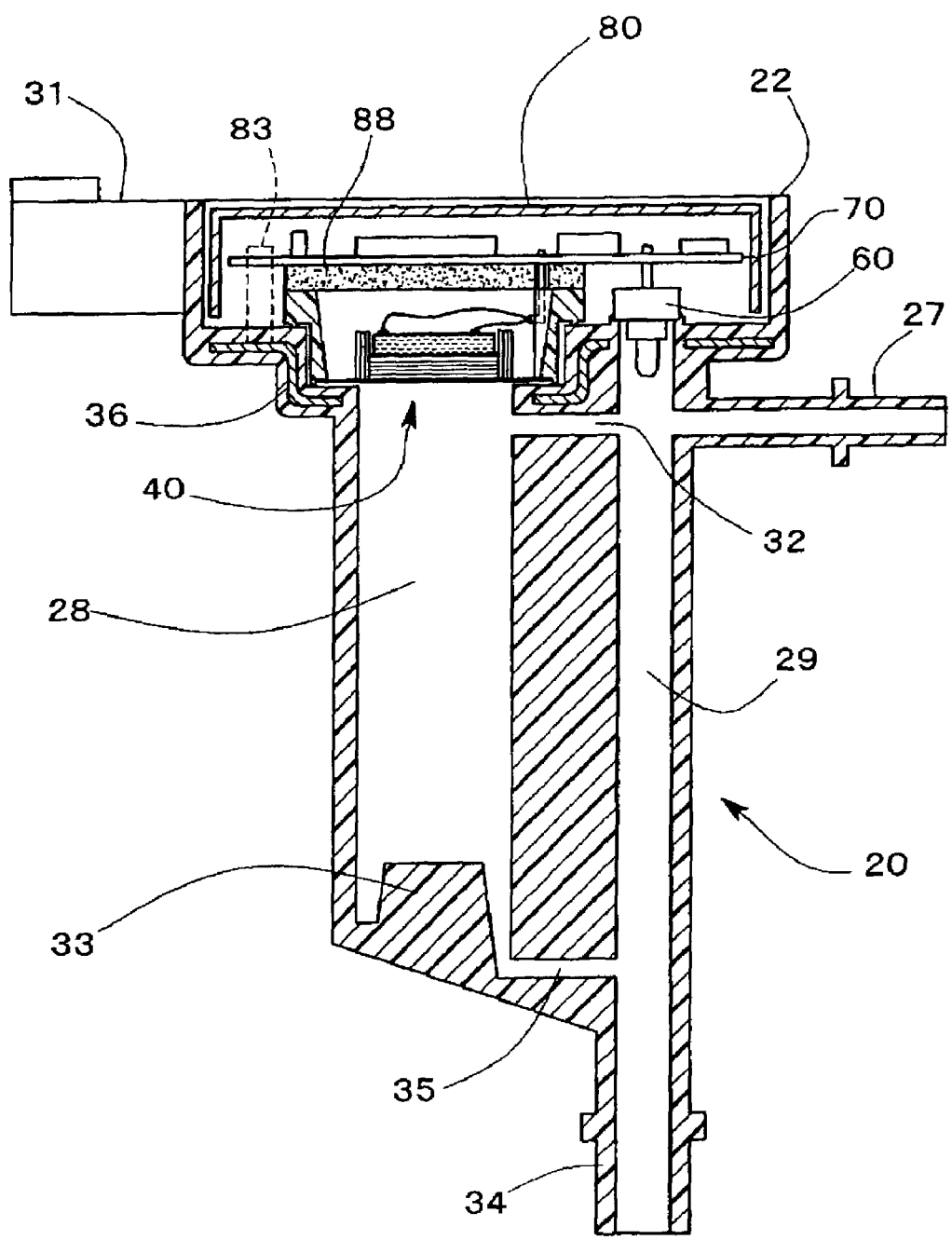
FIG. 2 is a sectional view showing the structure of the gas sensor 10.

The structure of the flow path will be described in detail with reference to FIG. 2 showing a vertical section of the gas sensor 10. FIG. 2 is a sectional view of the gas sensor 10 taken along a plane which includes the axis of the introduction path 27 and the axis of the detecting-element assembly 40. Notably, the gas sensor 10 is finally covered with resin (e.g., urethane resin) through molding. However, for clarification of illustration, FIG. 2 does not show the molding resin which covers the entire gas sensor 10. As shown in FIG. 2, in terms of flow path, the interior of the flow path formation member 20 is divided into the introduction path 27, the measuring chamber 28, and the bypass 29. These flow path portions can be readily formed through molding by use of a movable mold. The introduction path 27 communicates with the bypass 29 perpendicularly and with the measuring chamber 28 via an inlet hole 32. An outlet 34 is formed at a lower end portion of the bypass 29. A gas which contains gasoline vapor and is introduced through the introduction path 27 is discharged from the outlet 34. In the present embodiment, the discharged gas is led to an intake path of an internal combustion engine through an unillustrated hose. The mounting hole 25 in which the thermistor 60 is mounted is formed at an end portion of the bypass 29 opposite the outlet 34. Therefore, the thermistor 60 detects the temperature of a gas introduced through the introduction path 27, according to a predetermined law.

An upper portion of the measuring chamber 28 communicates with the recess 24 in which the detecting-element assembly 40 is mounted. A reflective portion 33 for reflecting ultrasonic waves is formed at a lower portion of the measuring chamber 28. The function of the reflective portion 33 will be described later. The reflective portion 33 is raised by a predetermined height (several millimeters in the present embodiment) from a bottom portion of the measuring chamber 28. A groove around the reflective portion 33 is connected to the bypass 29 via a discharge path 35 which communicates with the bottom portion of the measuring chamber 28. Thus, the gas which is introduced through the introduction path 27 and the inlet hole 32 fills the measuring chamber 28 and flows out at a predetermined ratio to the bypass 29 via the discharge path 35. Notably, since the discharge path 35 is provided at the bottom portion of the measuring chamber 28, water droplets and oil droplets formed through condensation of water vapor and gasoline vapor in the measuring chamber 28 are drained through the discharge path 35. In order to facilitate drainage of liquid collected in the groove around the reflective portion 33, the groove is sloped downward toward the discharge path 35.

As described above, the mounting recess 24—which has an opening communicating with the measuring chamber 28—and the mounting hole 25—which is used to mount a thermistor—are formed on the housing portion 22, which is formed at an upper portion of the flow path formation member 20. A metal plate 36 is embedded in the housing portion 22 through insert molding. The metal plate 36 is embedded in the bottom of the housing portion 22 while assuming a shape resembling the shape of the bottom. The metal plate 36 has a cut-and-raised portion 83 for establishing electrical connection. As shown in FIG. 1, after insert molding, the cut-and-raised portion 83 is in a condition to stand within the interior of the housing portion 22. When the electronic circuit board 70 is to be mounted, the cut-and-raised portion 83 is inserted into a connection hole 72 formed in the board 70. A land connected to a grounding line is provided around the connection hole 72. The cut-and-raised portion 83 is soldered to the land.

A protrusion for use with a terminal is provided at one of four inside corners of the housing portion 22 adjacent to the cut-and-raised portion 83 and is also used as a support base for supporting the electronic circuit board 70 which is placed thereon. A connector 31 for transmitting and receiving electric signals is formed at the outside of the protrusion. The terminals of the connector 31 extend through the wall of the housing portion 22 at the position corresponding to the protrusion. The connector 31 has three terminals on the inlet side thereof. Two opposite terminals of the three are the GND terminal and the Vcc terminal which are connected to power lines (ground and DC voltage) for supplying power to the gas sensor 10 from the outside, and the central terminal is the SGNL terminal connected to a signal output line of the gas sensor 10 (see FIG. 5). These terminals of the connector 31 become four terminals on the side of the housing portion 22. This is because the GND terminal to be connected to the ground line is forked. One end of the forked terminal (GND1 terminal in FIG. 5) is soldered to the electronic circuit board 70, and the other end of the forked terminal (GND2 terminal in FIG. 5) extends upward and is inserted, when the casing 80 is to be installed, into a connection hole 85 (see FIG. 1) provided in the casing 80 at the corresponding position. The inserted end of the forked terminal is soldered or brazed to the casing 80. As a result, the entire casing 80 is electrically connected to the ground line. At the remaining two inside corners of the housing portion 22, unillustrated support bases are formed for the purpose of supporting the electronic circuit board 70 which is placed thereon.

Figure 3:
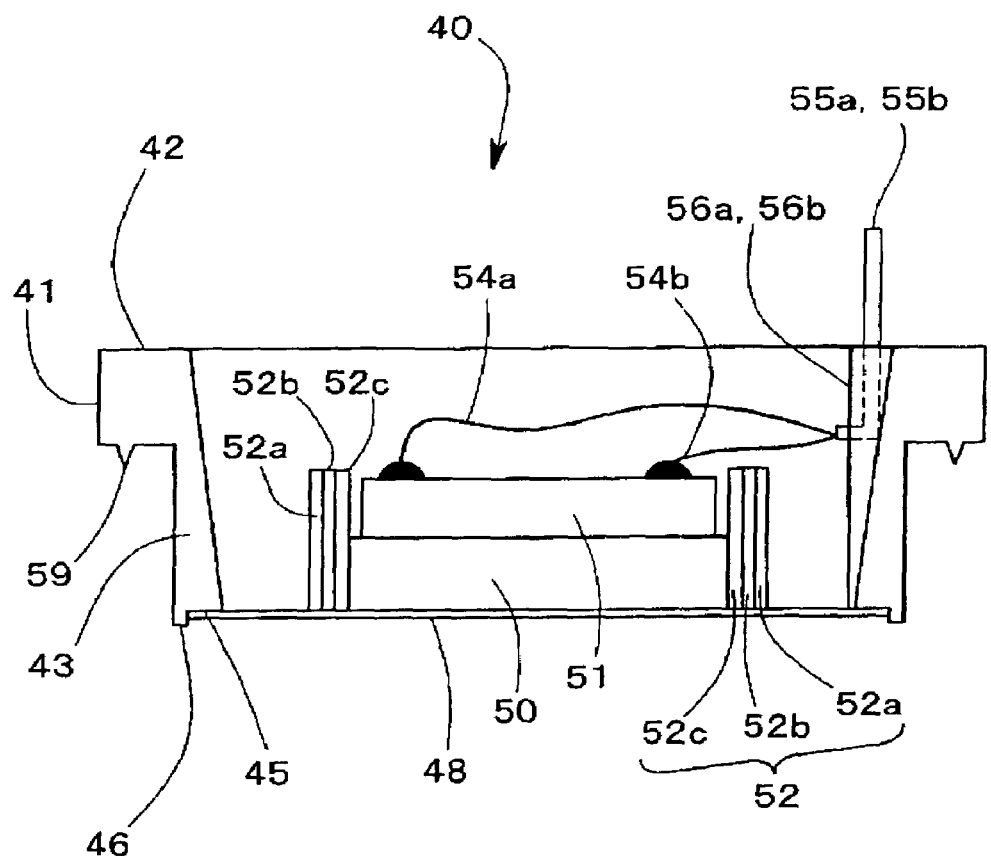
FIG. 3 is a sectional view showing the structure of a detecting-element assembly 40.

(C) Structure of Detecting-element Assembly 40:

FIG. 3 is a sectional view showing the structure of the detecting-element assembly 40. As shown in FIG. 1, the detecting-element assembly 40 assumes a disk-like shape, for the following reason: after a piezoelectric element 51 and other elements, which will be described later, are housed in an element casing 42 having a flange portion 41 and formed from a synthetic resin, the element casing 42 is filled with urethane resin. The flange portion 41 of the element casing 42 has a diameter greater than that of the recess 24 formed in the housing portion 22. A casing body portion 43 extending downward from the flange portion 41 has a diameter smaller than that of the recess 24. In an isolated state of the element casing 42, the casing body portion 43 opens downward, and a stepped portion 46 is formed on an end face 45 of the casing body portion 43 along the outer edge thereof. In the process of manufacture, a circular protective film 48 formed from a gasoline-resistant material is bonded to the end face 45 in such a manner as to be located inside the stepped portion 46. Since the stepped portion 46 is shaped in such a manner as to render the surface tension of liquid greater than that at a central portion of the protective film 48, liquid preferentially adheres thereto. The stepped portion 46 is of such a simple structure as to extend from the lower end of the casing body portion 43. The stepped portion 46 protrudes along the entire circumference of the end face 45. Alternatively, the stepped portion 46 may protrude along such a partial circumference as to provide a lyophilic property. The stepped portion 46 surrounds the circumferential edge of the protective film 48 such that the circumferential edge is not exposed to the outside. Thus, even when the detecting-element assembly 40 impinges on another member at the time of attachment, the circumferential edge of the protective film 48 is not susceptible to a large force. Also, the circumferential edge of the protective film 48 is not susceptible to a large force induced by a gas flow. Therefore, the protective film 48 is unlikely to come off, thereby preventing a problem of direct exposure of the interior of the detecting-element assembly 40 to a gas flow and a deterioration in the characteristics of the piezoelectric element 51. The end face 45 formed on the inside of the stepped portion 46 is formed such that the difference between its outside diameter and the diameter of the protective film 48 is very small. Thus, when the protective film 48 is fitted to an open lower end from underneath, the stepped portion 46 serves as a guide for positioning the protective film 48, whereby the center misalignment between the protective film 48 and the element casing 42 can fall within a predetermined range of variation. Therefore, a positioning jig for use in attaching the protective film 48 to the open lower end of the element casing 42 is unnecessary, thereby facilitating work. Instead of forming the stepped portion 46 integrally with the element casing 42, a separate member to be attached to the open lower end of the element casing 42 may be employed so as to hold the protective film 48 between the member and the lower end of the element casing 42.

A columnar, acoustic matching plate 50 is bonded to the protective film 48 at the center thereof. The piezoelectric element 51, which is an ultrasonic generation element, is bonded to the upper surface of the acoustic matching plate 50. The acoustic matching plate 50 is adapted to efficiently transmit vibrations of the piezoelectric element 51 into the air (the measuring chamber 28 in the present embodiment) via the protective film 48. Since sonic waves and ultrasonic waves tend to be reflected where the density of a medium differs, the piezoelectric element 51 is not directly bonded to the protective film 48, but is bonded via the acoustic matching plate 50, so that vibrations of the piezoelectric element 51 are efficiently transmitted as ultrasonic waves into the measuring chamber 28. In the present embodiment, the acoustic matching plate 50 is formed such that a number of small glass beads are solidified together by means of an epoxy resin. A tubular member 52 is disposed in such a manner as to surround the acoustic matching plate 50 and the piezoelectric element 51. The tubular member 52 is formed in the following manner. A polyethylene terephthalate film 52a and a copper foil 52c are bonded together via a bonding layer 52b. The resultant laminate is rolled into a cylindrical shape such that the copper foil 52c comes inside, and mating ends are bonded together in an overlapped condition. Since the inside diameter of the tubular member 52 is substantially equal to the outside diameter of the acoustic matching plate 50, the tubular member 52 comes in close contact with the outer circumferential surface of the acoustic matching plate 50. However, these two members are not bonded together.

The piezoelectric element 51 is a piezoelectric or electrostrictive element formed into a columnar shape. The element is cut out while the lattice orientation is adjusted such that, when voltage is applied to electrodes formed on the axially upper and lower faces of the element, deformation arises only along the axial direction. As will be described later, in the present embodiment, the piezoelectric element 51 functions as a transmitter for transmitting ultrasonic waves into the measuring chamber 28 and as a receiver for receiving ultrasonic waves and outputting electric signals. As a matter of course, a gas sensor may be formed such that a transmitting element and a receiving element are provided separately. The piezoelectric element 51 can be of piezoelectric ceramic or crystal such as quartz as appropriate. Electrodes are not illustrated, but may be formed on the upper and lower faces of the piezoelectric element 51 through vapor deposition or a like process or through bonding of thin metal plates.

As shown in FIG. 3, the element casing 42 has a section whose shape resembles the inverted letter "L." The inner surface of the element casing 42 is tapered at a predetermined angle (about 11 degrees in the present embodiment) with respect to the vertical plane. Therefore, the wall of the casing body portion 43 increases in thickness downward; i.e., toward the protective film 48. As a result, the casing body portion 43 of the element casing 42 is formed such that its wall merged with the flange portion 41 is thin to thereby provide flexibility and such that its lower end face provides a sufficient area for bonding the protective film 48 thereto. The element casing 42 is formed into a substantially cylindrical shape except that portions where terminals 55a and 55b are embedded protrude inward. These protrusions 56a and 56b have the terminals 55a and 55b embedded therein through insert molding. The terminals 55a and 55 are each bent into a shape resembling the letter "L." The lower end of each of the terminals 55a and 55b protrudes inward from the inner surface of the casing body portion 43. Lead wires 54a and 54b are soldered to the lower ends of the terminals 55a and 55b, respectively. After the lead wires 54a and 54b of the piezoelectric element 51 are thus connected, urethane resin is filled into the element casing 42. Notably, the upper ends of the terminals 55a and 55b protrude upward from the upper surface of the element casing 42. When the electronic circuit board 70 is to be installed above the terminals 55a and 55b, the terminals 55a and 55b are inserted into corresponding connection holes formed in the electronic circuit board 70 and soldered to corresponding lands provided around the holes.

Figure 4:
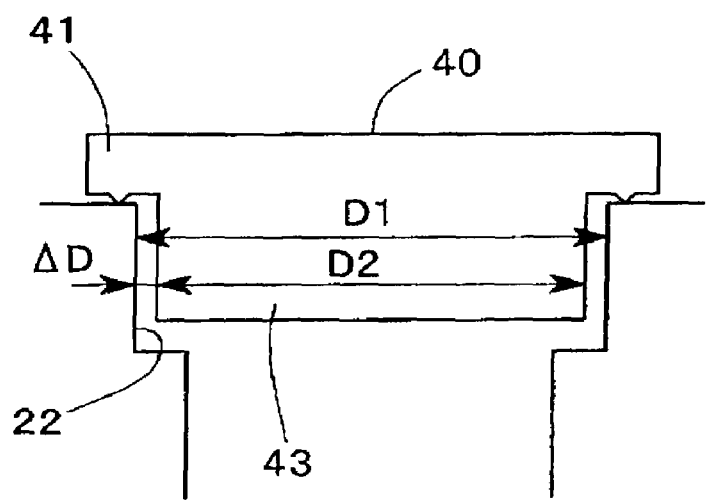
FIG. 4 is a sectional view showing the structural relationship between the detecting-element assembly 40 and a housing portion 22.

The element casing 42 has a circumferential protrusion 59 formed on the lower surface of the flange portion 41 substantially at the center. The protrusion 59 is melted through ultrasonic welding so as to fixedly join the flange portion 41 to the housing portion 22. FIG. 4 shows a state in which the flange portion 41 is fixedly joined to the bottom surface of the housing portion 22. The inside diameter D1 of the recess 24 of the housing portion 22 and the outside diameter D2 of the element casing 42 of the detecting-element assembly 40 are determined so as to differ by 2 mm or more (D1≧D2+2). As a result, the clearance ΔD between the outer circumferential surface of the casing body portion 43 and the inner circumferential surface of the recess 24 is about 1 millimeter on average. Employment of a clearance ΔD of 1 mm or more has been proved to be effective for reducing reverberations, which will be described later. Also, employment of a clearance ΔD of 1 mm or more prevents oil sludge and dust, which have entered the measuring chamber 28, from collecting in the clearance, thereby avoiding a problem which could result from collected foreign matter during long-term use.

(D) Electronic Circuit Board 70, its Circuitry, and Method for Determining Gas Concentration:

Next, the structure and installation of the electronic circuit board 70 will be described. The electronic circuit board 70 is configured such that circuit patterns are formed on a glass epoxy substrate through etching or the like and such that lands and through-holes are provided where components are to be mounted. As described previously, connection holes are formed in the electronic circuit board 70 at those positions where the terminals of the detecting-element assembly 40, the terminals of the thermistor 60, the terminals of the connector 31, and the cut-and-raised portion 83 are connected. The connection holes are shaped so as to match the corresponding terminals, and surrounded by corresponding land patterns. Therefore, the completed electronic circuit board 70 is configured such that signal processing devices, for example, a signal processing integrated circuit (IC), resistors, and capacitors, are mounted at predetermined positions. The electronic circuit board 70 is installed in the housing portion 22 in which the detecting-element assembly 40 and the thermistor 60 are already installed, followed by soldering. The electric circuitry is thus completed. In manufacture of the gas sensor 10, resin molding is performed at the final stage as will be described later in the "method for manufacturing gas sensor" section.

In relation to soldering of terminals to the electronic circuit board 70, the electronic circuit board 70 does not have a land corresponding to the outermost GND2 terminal (see FIG. 5) among the terminals of the connector 31. The GND2 terminal merely extends through a through-hole formed in the electronic circuit board 70. The GND2 terminal extending through the through-hole formed in the electronic circuit board 70 is inserted into the connection hole 85 formed in the casing 80 and soldered or brazed to the casing 80.

Figure 5:
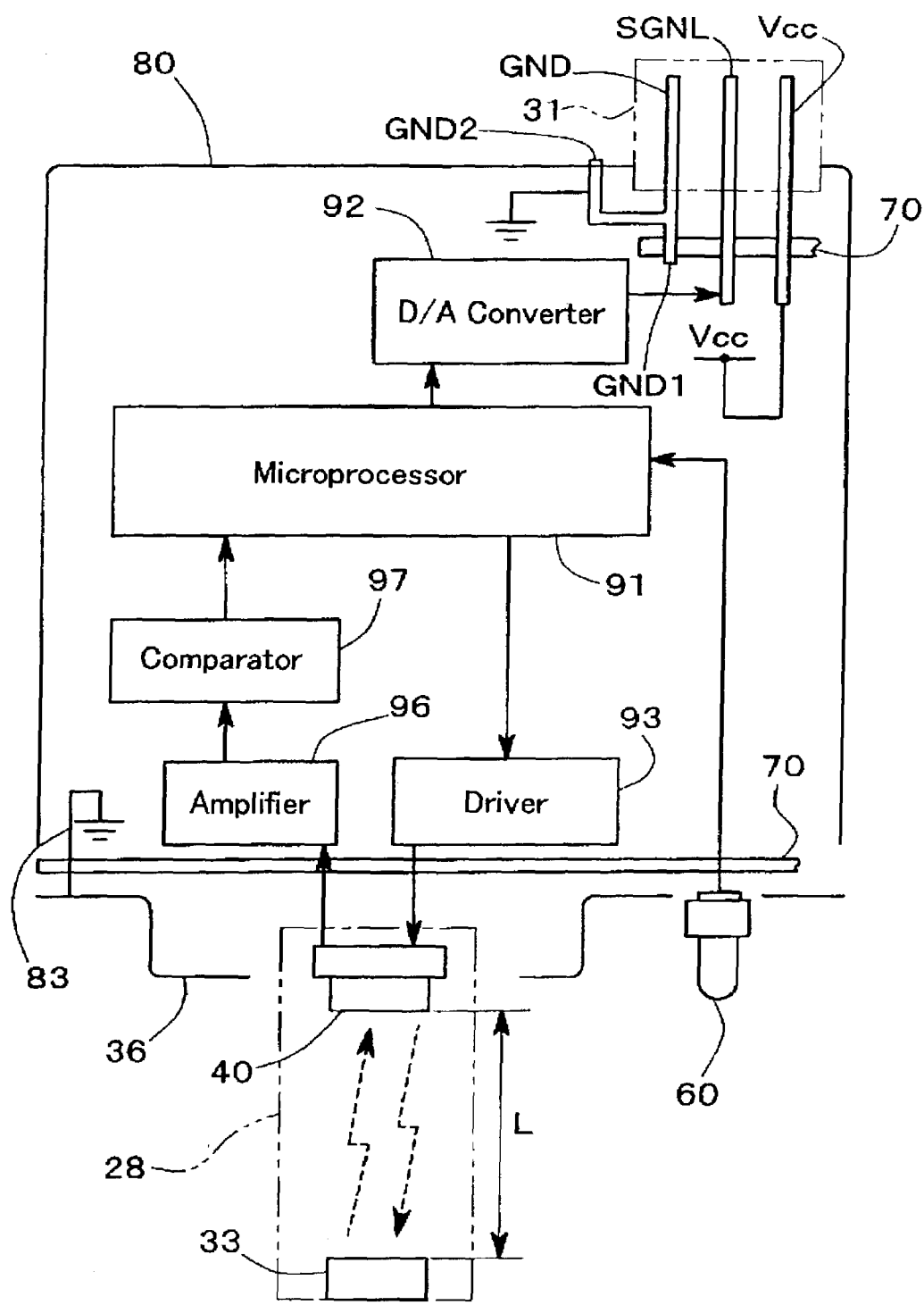
FIG. 5 is an schematic diagram showing the electrical configuration of an electronic circuit board 70.

The block diagram of FIG. 5 shows the electrical configuration of the thus-completed gas sensor 10. As shown in FIG. 5, the electronic circuit board 70 includes a microprocessor 91 as a central component as well as circuit elements connected to the microprocessor 91, such as a digital-to-analog converter (D/A converter) 92, a driver 93, and a comparator 97 to which an amplifier 96 is connected. The thermistor 60 is directly connected to an analog input port PAP of the microprocessor 91. The driver 93 and the amplifier 96 are connected to the detecting-element assembly 40.

The driver 93 is a circuit for driving the piezoelectric element 51 of the detecting-element assembly 40 for a predetermined time upon reception of an instruction from the microprocessor 91. Upon reception of an instruction from the microprocessor 91, the driver 93 outputs a plurality of rectangular waves. Upon reception of signals of rectangular waves output from the driver 93, the piezoelectric element 51 vibrates and functions as a transmitter, thereby transmitting ultrasonic waves into the measuring chamber 28.

Figure 6:
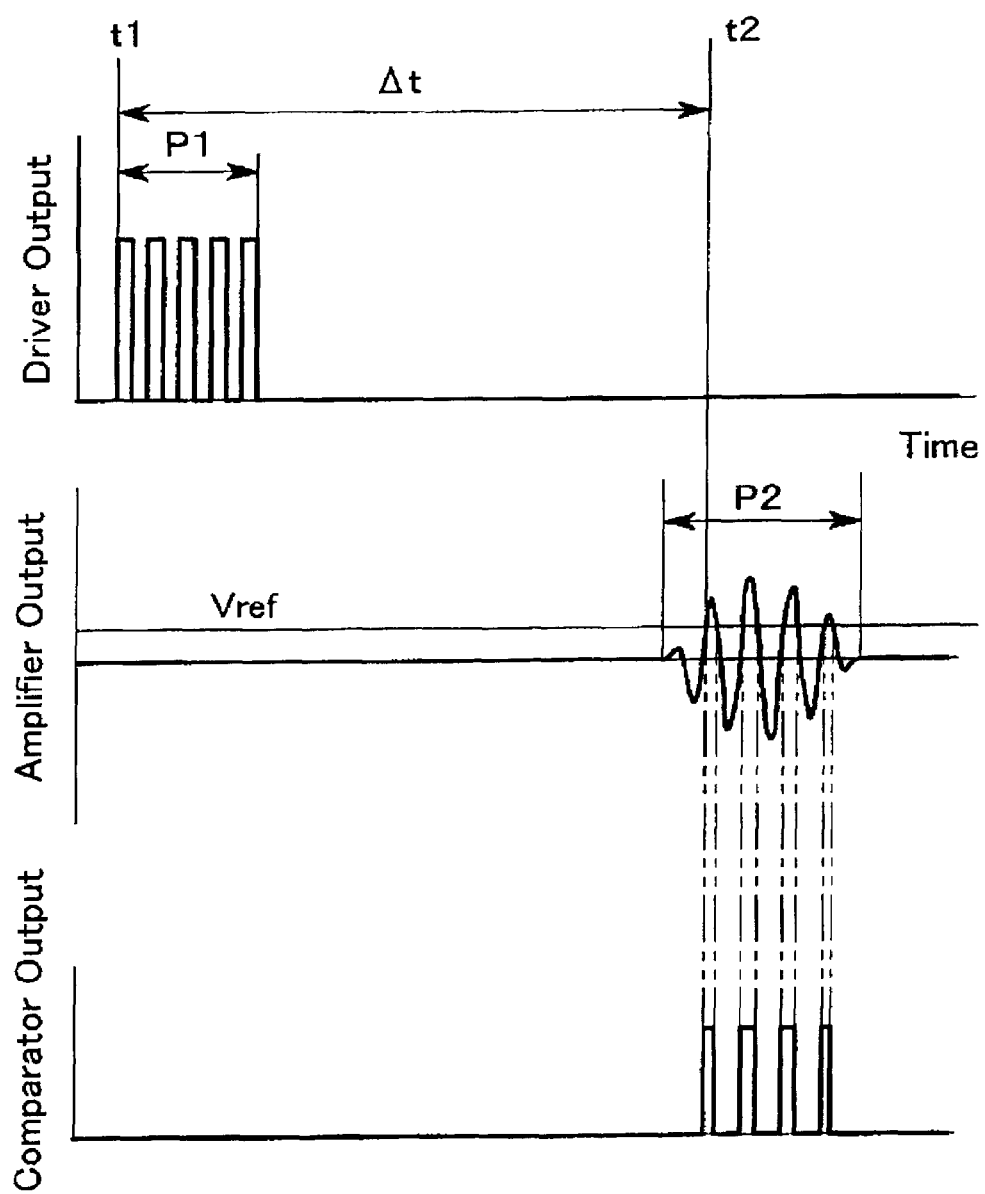
FIG. 6 shows explanatory time-charts for explaining the principle of determining gas concentration by use of ultrasonic waves.

Ultrasonic waves transmitted into the measuring chamber 28 propagate rectilinearly while maintaining relatively high directivity and reflectively return from the reflective portion 33 at the bottom of the measuring chamber 28. When the reflected ultrasonic waves reach the protective film 48, its vibrations are transmitted to the piezoelectric element 51 via the acoustic matching plate 50, and the piezoelectric element 51 now functions as a receiver and outputs electric signals corresponding to the vibrations. This is shown in FIG. 6. In FIG. 6, period P1 is a period when the driver 93 outputs signals, and the piezoelectric element 51 functions as a transmitter, whereas period P2 is a period when vibrations induced by ultrasonic waves reflected from the reflective portion 33 are transmitted to the piezoelectric element 51, and the piezoelectric element 51 functions as a receiver.

Signals output from the piezoelectric element 51 which functions as a receiver are input to the amplifier 96 and amplified. An output from the amplifier 96 is input to the comparator 97 and compared with a previously prepared threshold value Vref. The threshold value Vref is a level for discriminating a false signal which is output from the amplifier 96 under the influence of noise or the like. In addition to a false signal which is output under the influence of noise, a false signal is also output under the influence of reverberations held in the detecting-element assembly 40 itself.

The comparator 97 compares a signal received from the amplifier 96 with the threshold value Vref and inverts its output when the amplitude of vibration received by the piezoelectric element 51 exceeds a predetermined value. Monitoring an output from the comparator 97, the microprocessor 91 measures time Δt between the timing of output of the first ultrasonic wave from the piezoelectric element 51 (timing t1 in FIG. 6) and the timing of inversion of output from the comparator 97 (timing t2 in FIG. 6), thereby obtaining time required for the ultrasonic wave to make a round trip over the distance L to the reflective portion 33 in the measuring chamber 28. Ultrasonic waves are known to propagate through a certain medium at speed C that is expressed below by Eq. (1).

$$C = \sqrt{\frac{RT \sum C_{pn} X_n}{\sum C_{vn} X_n \sum M_n X_n}} \quad (1)$$

Eq. (1) is a general expression which holds with respect to a mixed gas of a plurality of components, and variable n is a suffix representing the n'th component. Therefore, $C_{pn}$ represents specific heat at constant pressure of the n'th component of a gas present in the measuring chamber 28; $C_{vn}$ represents specific heat at constant volume of the n'th component of a gas present in the measuring chamber 28; $M_n$ represents the molecular weight of the n'th component; and $X_n$ represents the ratio of concentration of the n'th component. Also, R is gas constant, and T is the temperature of a gas present in the measuring chamber 28. Since specific heat and other factors of a gas are known, the propagation speed C depends on the temperature T and ratio-of-concentration $X_n$ of a gas present in the measuring chamber 28. By use of the distance L between the piezoelectric element 51 and the reflective portion 33, the propagation speed C of ultrasonic waves is represented by $$C = 2 \times L / \Delta t \quad (2)$$

Thus, through measurement of Δt, the ratio-of-concentration $X_n$; i.e., gasoline concentration, can be obtained. Notably, in the present embodiment, the concentration of gasoline vapor is determined; however, when concentration is known, the sensor can be used to obtain the temperature T or propagation distance L.

The microprocessor 91 performs arithmetic operations at high speed according to the above-mentioned expressions and outputs a signal corresponding to the thus-obtained gasoline concentration to the D/A converter 92. This signal is output to an external device via the SGNL terminal of the connector 31. In the present embodiment, the SGNL terminal is connected to a computer (ECU) which controls fuel injection quantity of an internal combustion engine. The signal corresponding to gasoline concentration is read into the ECU and is used in the process of correcting fuel injection quantity in consideration of the quantity of gasoline purged from a canister. Notably, FIG. 5 does not show lines related to power supply, but the microprocessor 91 and other devices are each connected to a power line of supplying DC voltage Vcc and to the ground (ground line). As described previously, the ground line is connected to the metal plate 36, which is insert-molded in the housing portion 22 of the flow path formation member 20, and to the casing 80. FIG. 5 schematically shows these members, but in actuality the metal plate 36 and the casing 80 (see FIG. 1) jointly form a box member (see FIG. 2) that covers the detecting-element assembly 40, and are maintained at the same electric potential to thereby establish an electromagnetic shield in terms of electricity. Therefore, the detecting-element assembly 40 and electronic circuit board 70 which are housed within the box member are effectively protected against external noise.

(E) Action and Effect of the Embodiment:

The above-described gas sensor 10 of the present embodiment can accurately determine the concentration of gasoline vapor in a gas introduced into the measuring chamber 28 of the flow path formation member 20 by use of ultrasonic waves. Furthermore, the gas sensor 10 of the present embodiment is configured in the following manner: the detecting-element assembly 40 is attached to the measuring chamber 28 via the flange portion 41; the flange portion 41 is located opposite the measuring chamber 28 with respect to the piezoelectric element 51; and the casing body portion 43 in which the piezoelectric element 51 is housed protrudes from the flange portion 41 toward the measuring chamber 28. As a result, the following effects are obtained.

(1) Noise stemming from reflection of ultrasonic waves which leak from the piezoelectric element 51 into the interior of the detecting-element assembly 40 can be reduced.

(2) Noise stemming from ultrasonic waves which propagate through the flow path formation member 20 can be reduced.

Effect (1) will be described in detail. Ideally, the piezoelectric element 51 vibrates only in the axial direction to thereby transmit ultrasonic waves only toward the measuring chamber 28. However, in actuality, ultrasonic waves which propagate to the interior of the detecting-element assembly 40 are present. Propagating through the interior of the detecting-element assembly 40, the ultrasonic waves reach the flange portion 41 and reflectively return from the joint between the flange portion 41 and the housing portion 22. In the detecting-element assembly 40, the thus-reflected ultrasonic waves appear as noise in the form of reverberations. Specifically, even after the driver 93 stops issuing transmission signals, the piezoelectric element 51 vibrates for a predetermined period of time. In this case, if the acoustic level of ultrasonic waves reflectively returning from the joint between the flange portion 41 and the housing portion 22 is high, the reflected ultrasonic waves are detected as reverberations. In the present embodiment, the flange portion 41 is integrated with one end of the casing body portion 43, whereby the casing body portion 43 is joined to the housing portion 22 via the flange portion 41. Thus, the distance between the piezoelectric element 51 and the joint is elongated, whereby the acoustic level of ultrasonic waves reflectively returning from the joint can be damped sufficiently. Therefore, reverberations stemming from reflection from the joint can be reduced, thereby enhancing the accuracy of detection.

Effect (2) will be described in detail. Ultrasonic waves transmitted from the end face of the detecting-element assembly 40 propagate within the measuring chamber 28 toward the reflective portion 33 and reflectively return from the reflective portion 33. Ultrasonic waves exhibit high directivity, but have a predetermined extent. Thus, not all ultrasonic waves propagate toward and reflectively return from the reflective portion 33. Some ultrasonic waves impinge on, for example, the inner wall of the flow path formation member 20 and propagate through the flow path formation member 20. A part of such ultrasonic waves reach the detecting-element assembly 40 after propagation through the flow path formation member 20. However, in the present embodiment, the detecting-element assembly 40 is joined to the housing portion 22 at the flange portion 41 thereof to thereby elongate the path of propagation, and ultrasonic waves cannot propagate to the detecting-element assembly 40 unless they turn the direction of propagation at the joint between the flange portion 41 and the housing portion 22. Therefore, the piezoelectric element 51 of the detecting-element assembly 40 is hardly susceptible to the influence of ultrasonic waves propagating through the flow path formation member 20.

Furthermore, according to the present embodiment, as described previously, the inside diameter of the recess 24 provided on the housing portion 22 is 2 millimeters or more greater than the outside diameter of the casing body portion 43 of the detecting-element assembly 40. As a result, the average clearance between the two is 1 millimeter or more, thereby providing the following effects.

(3) The influence of reverberations is reduced.

(4) Collection of foreign matter or the like is prevented, thereby preventing a change in acoustic characteristics.

Figure 7:
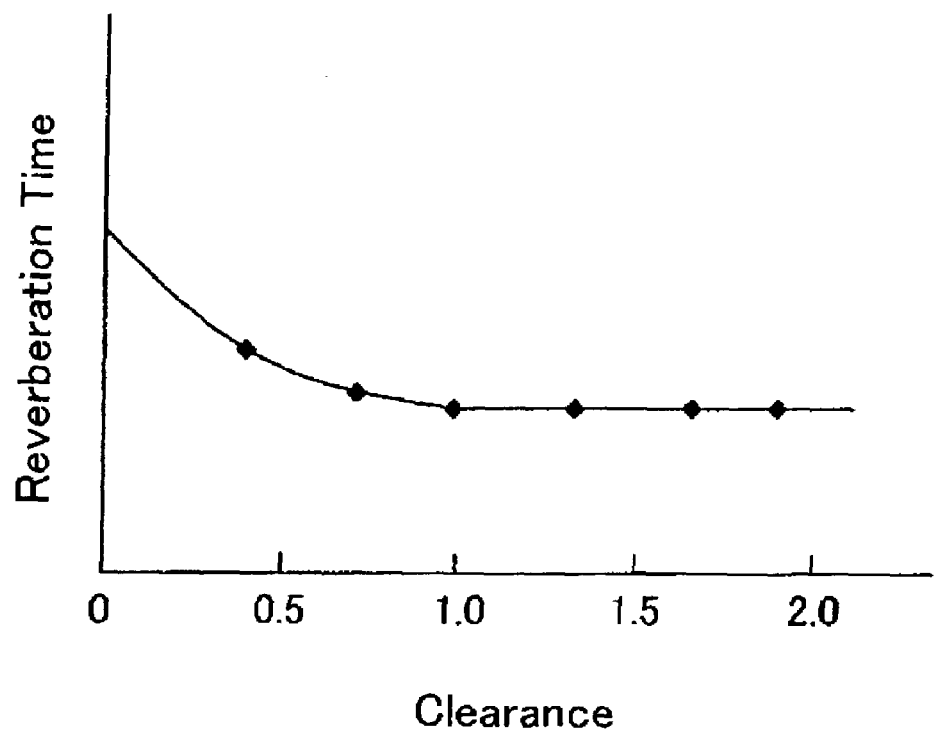
FIG. 7 is a graph showing the experimentally obtained relationship between reverberation and clearance in the embodiment.

These effects will be described in detail. As shown in FIG. 7, as the clearance between the two increases, the influence of reverberations reduces. In the graph of FIG. 6, reverberation time in FIG. 7 is the time between end of period P1 during which the driver 93 outputs signals and a point of time when the amplitude of vibrations remaining in the piezoelectric element 51 drops below a predetermined level. As shown in FIG. 7, at a clearance less than 1 millimeter, the reverberation level is not sufficiently reduced. By contrast, at an average clearance equal to or greater than 1 millimeter, reverberations are sufficiently reduced. Also, at a clearance equal to or greater than 1 millimeter, foreign matter, such as oil sludge, which tends to become mixed in a gas in a path extending to a canister is not collected, thereby preventing a problem associated with collected foreign matter, for example, a change in acoustic characteristics.

Figure 8:
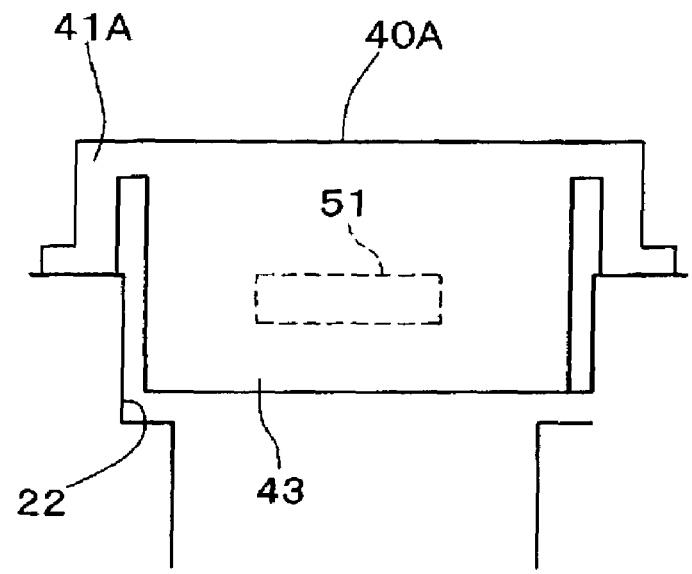
FIG. 8 is an explanatory view showing a first modified example of the embodiment.
Figure 9:
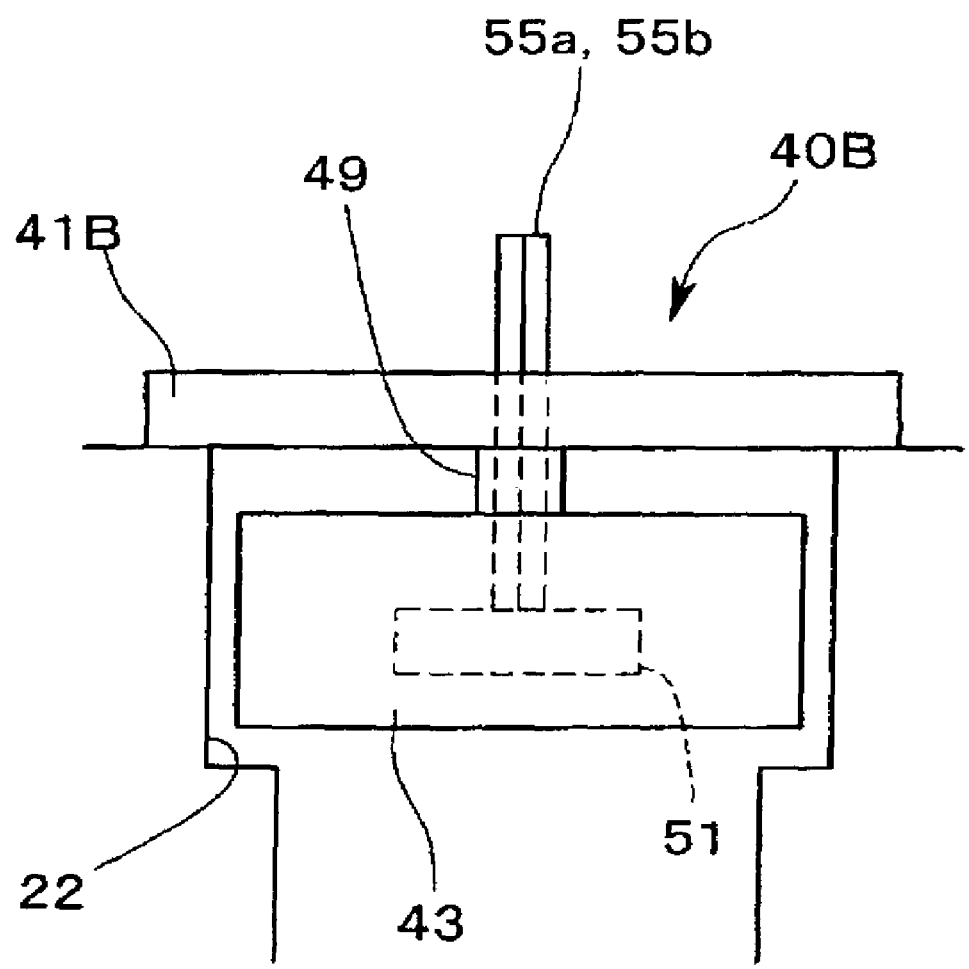
FIG. 9 is an explanatory view showing a second modified example of the embodiment.

(F) Modified Examples:

Modified examples of the present invention will next be described. FIGS. 8 and 9 are sectional views showing modified examples of a detecting-element assembly. A detecting-element assembly 40A according to the modified example of FIG. 8 assumes substantially the same configuration as that of the above-described embodiment. In this modified example, a flange portion 41A is not formed flatly at one end of the casing body portion 43, but is formed such that, as shown in FIG. 8, an outer circumferential end portion is curved into a shape resembling the letter "L." As a result, as viewed from the position of welding to the housing portion 22, the linear distance to the piezoelectric element 51 housed in the casing body portion 43 is the same as that in the first embodiment; however, the length of a path to the piezoelectric element 51 becomes longer. Therefore, the piezoelectric element 51 is not susceptible, to a greater extent, to the influence of ultrasonic waves which leak from the piezoelectric element 51 into the interior of the element casing 42 and reflectively return from the joint between the flange portion 41A and the housing portion 22.

As shown in FIG. 9, a flange portion 41B may be joined to the casing body portion 43 via a support 49 provided at the center of the casing body portion 43. Also in this case, the path extending from the piezoelectric element 51 to the joint can be elongated. In the configuration of FIG. 9, the terminals 55a and 55b may be provided in such a manner as to extend through the support 49.

Figure 10:
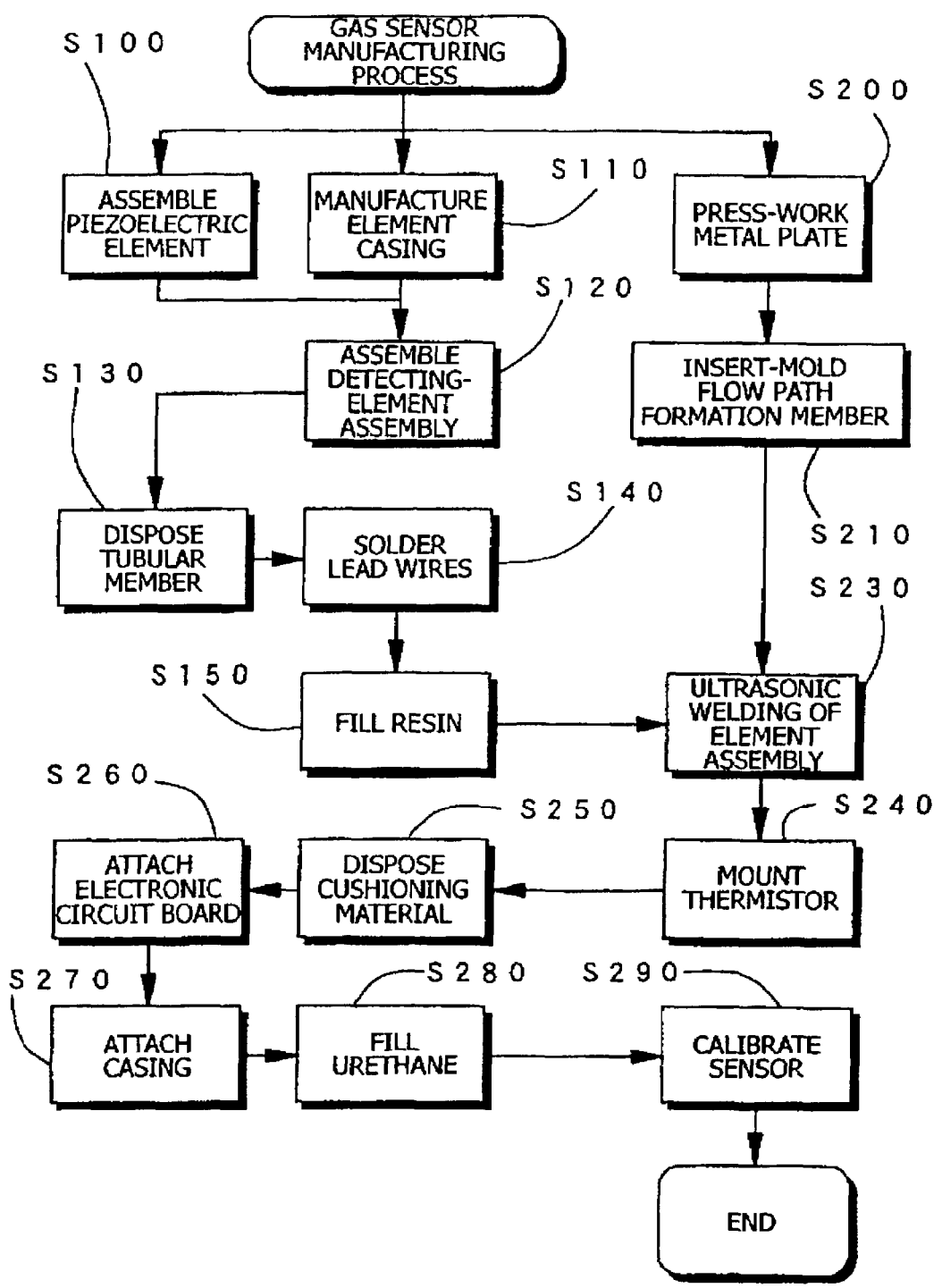
FIG. 10 is a process chart showing a method for manufacturing the gas sensor 10 in the embodiment.
Figure 11:
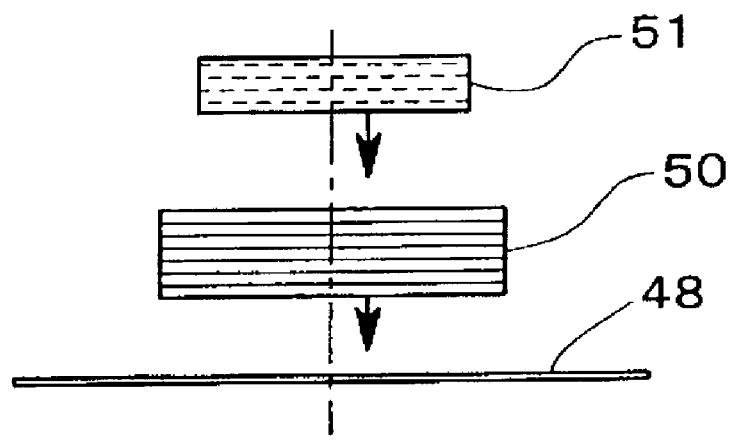
FIGS. 11(A) and (B) are explanatory views showing the manner of assembling a piezoelectric element assembly.
Figure 11:
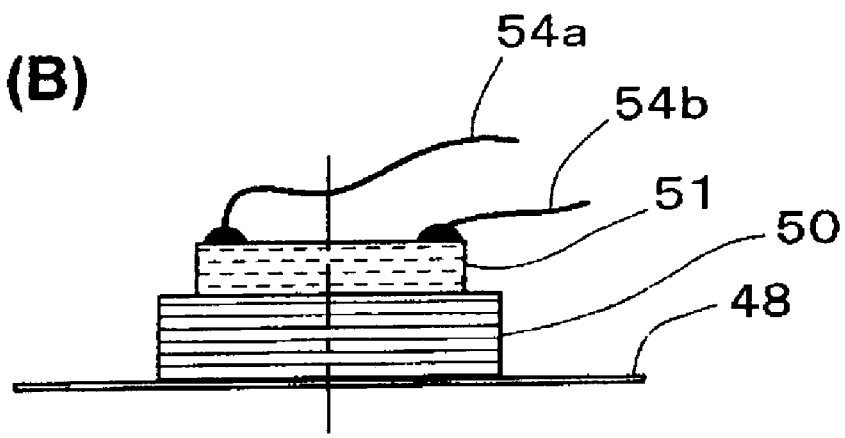

(G) Method for Manufacturing Gas Sensor:

Next, a method for manufacturing the gas sensor 10 according to the present embodiment will be described. FIG. 10 is a process diagram showing a process for manufacturing a gas sensor. As shown in FIG. 10, manufacture of the gas sensor 10 begins with assembly of a piezoelectric element (step S100). As shown in FIG. 11, in this step, the protective film 48 is cut into a predetermined shape (circular shape in the present embodiment), and the acoustic matching plate 50 is bonded to the center of the protective film 48. Furthermore, the piezoelectric element 51 is concentrically bonded to the acoustic matching plate 50. At this time, a jig may be used for centering. FIG. 11(A) shows a state of bonding, and FIG. 11(B) shows a state after bonding. As shown in FIG. 11(B), after bonding, the lead wires 54a and 54b are connected to corresponding electrodes of the piezoelectric element 51 by means of, for example, soldering or discharge welding.

The element casing 42 for housing the thus-obtained piezoelectric element assembly in a sealed condition is prepared (step S110). As shown in FIG. 12(A), the element casing 42 is manufactured from a glass-filler-containing synthetic resin through injection molding. As a matter of course, cutting or a like process may be employed instead. The terminals 55a and 55b are insert-molded in the protrusions 56a and 56b formed on the inside of the element casing 42.

Next, the detecting-element assembly is assembled (step S120). In this step, first, the piezoelectric element assembly which was assembled in step S100 is attached to the element casing 42 which was manufactured in step S100. As shown in FIG. 12(B), this work is performed in the following manner: a peripheral portion of the protective film 48 is bonded to the lower end face 45 of the element casing 42 by use of an adhesive, whereby the piezoelectric element assembly is fixed in place. Since the stepped portion 46 is formed on the end face 45 along the outer edge thereof, the protective film 48 can be readily bonded to the end face 45 in place. In this state, as shown in FIG. 13(A), the tubular member 52 is inserted into the element casing 42 from its open end and fitted to the outer circumferential surface of the acoustic matching plate 50 (step S130). Prior to this assembly, the polyethylene terephthalate film 52a and the copper foil 52c are bonded together via the bonding layer 52b, and the resultant laminate is rolled to obtain the tubular member 52 whose inside diameter matches the outside diameter of the acoustic matching plate 50. The tubular member 52 is not bonded to the acoustic matching plate 50, but is merely fitted thereto.

In this state, the two lead wires 54a and 54b extending from the piezoelectric element 51 are connected to the terminals 55a and 55b, respectively, through soldering or a like process (step S140). As a result, as shown in FIG. 13(B), all of required components are attached to the detecting-element assembly 40. Next, urethane resin is filled into the element casing 42 from its open end (step S150). At this time, urethane resin which serves as filler is filled to such an extent as to cover the piezoelectric element 51 and the lead wires 54a and 54b extending from the upper end of the piezoelectric element 51 and as not to reach the upper end of the flange portion 41. FIG. 13(C) shows a state after filling.

In parallel with the above-described manufacture of the detecting-element assembly 40, the flow path formation member 20 is manufactured. This manufacturing process is represented by step S200 and subsequent steps. In manufacture of the flow path formation member 20, first, a metal plate is press-worked to obtain the metal plate 36 to be subjected to insert molding (step S200). The metal plate 36 used in the present embodiment is unitarily formed from a substantially rectangular metal plate (a tinned steel plate in the present embodiment) through press-working.

Next, the flow path formation member 20 is formed through insert-molding such that the metal plate 36 is embedded therein (step S210). The flow path formation member 20 is molded from a glass-filler-containing synthetic resin. When the flow path formation member 20 is to be molded, the metal plate 36 is held by use of a jig at a position where, after molding, the metal plate 36 is embedded in a bottom part of the housing portion 22. At this time, the terminals contained in the connector 31 are also embedded therein through insert molding.

Figure 14:
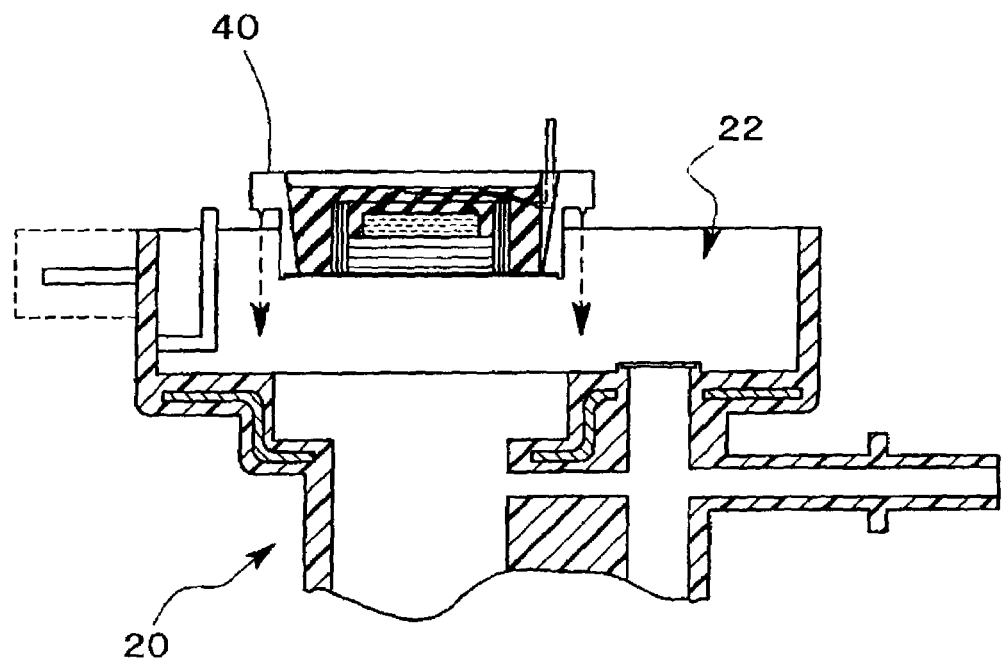
FIGS. 14(A) and (B) are explanatory views showing the manner of attaching the detecting-element assembly 40 to a housing portion 22 of a flow path formation member 20.
Figure 14:
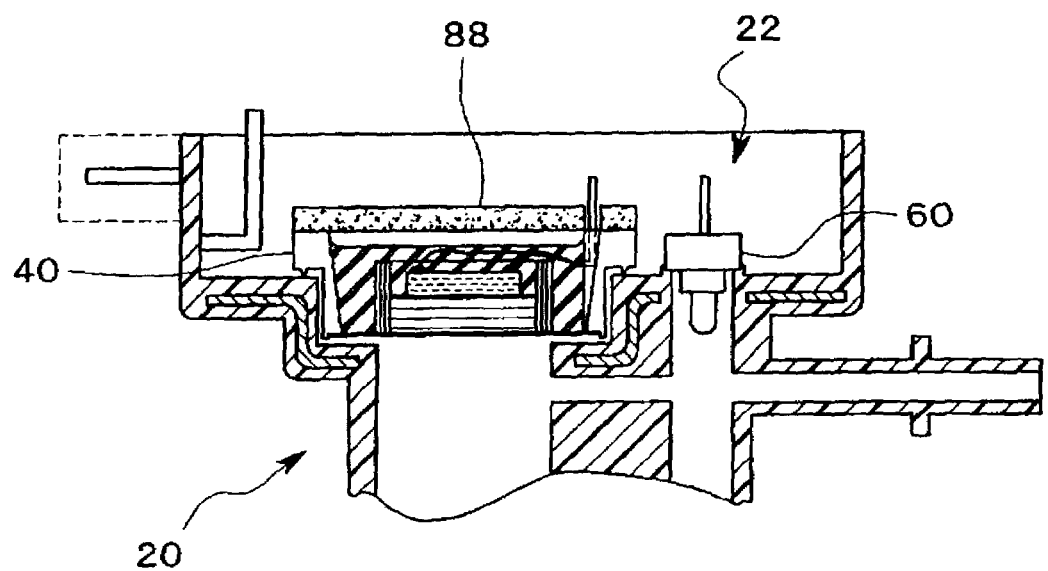

After the flow path formation member 20 is thus manufactured, the previously manufactured detecting-element assembly 40 is welded to the housing portion 22 (step S230). Welding is performed ultrasonically. Prior to this ultrasonic welding, being mounted on a predetermined jig, the detecting-element assembly 40 is concentrically positioned in the recess 24. Since the inside diameter D1 of the recess 24 and the outside diameter D2 of the casing body portion 43 differ by about 2–3 millimeters (D1>D2), concentric alignment of the recess 24 and the detecting-element assembly 40 forms an average clearance of about 1 millimeter between the inner surface of the recess 24 and the outer surface of the casing body portion 43 of the detecting-element assembly 40. While this concentric alignment is maintained, the detecting-element assembly 40 is vibrated at frequencies of an ultrasonic domain so as to strongly strike the lower surface of the flange portion 41 on a joint surface of the housing portion 22. Since the protrusion 59 is formed on the lower surface of the flange portion 41, force induced by ultrasonic vibrations concentrates on the protrusion 59. Concentration of mechanical energy on the protrusion 59 causes the protrusion 59 to be heated and then melted. As a result, the detecting-element assembly 40 is joined to the flow path formation member 20 such that the lower surface of the flange portion 41 is welded to the joint surface of the housing portion 22 while no clearance is left therebetween. FIGS. 14(A) and 14(B) show a state before and after attachment of the detecting-element assembly 40. Notably, welding may be performed by another process, such as hot plate welding.

At about the time of attachment of the detecting-element assembly 40, the thermistor 60 is mounted in the mounting hole 25 formed in the flow path formation member 20 (step S240). Subsequently, a cushioning material 88 is placed on the detecting-element assembly 40 (step S250). The cushioning material 88 is a foamed member having an outside diameter substantially equal to that of the detecting-element assembly 40 and a thickness of several millimeters. The cushioning material 88 has holes formed therein so as to allow the terminals 55a and 55b protruding upward from the detecting-element assembly 40 to extend therethrough. The cushioning material 88 has such a thickness as to be able to intervene between the detecting-element assembly 40 and the electronic circuit board 70, which will be attached in the subsequent step. The cushioning material 88 is adapted to prevent urethane resin to be filled in a later step, which will be described later, from filling the periphery of the detecting-element assembly 40.

After the cushioning material 88 is disposed, as shown in FIG. 15(A), the electronic circuit board 70 is housed from above in the housing portion 22 while the four members listed below are fitted into the corresponding connection holes formed in the board 70 (step S260).

Cut-and-raised portion 83 of the metal plate 36 which stands from a bottom part of the housing portion 22;
Terminals 55a and 55b protruding from the detecting-element assembly 40;
Terminals of the thermistor 60; and
Three terminals of the connector 31.

The above four members are fitted into the corresponding connection holes formed in the electronic circuit board 70. These members except the terminal 31d of the connector 31 are soldered to corresponding lands which are provided on the electronic circuit board 70 around the connection holes.

Figure 15:
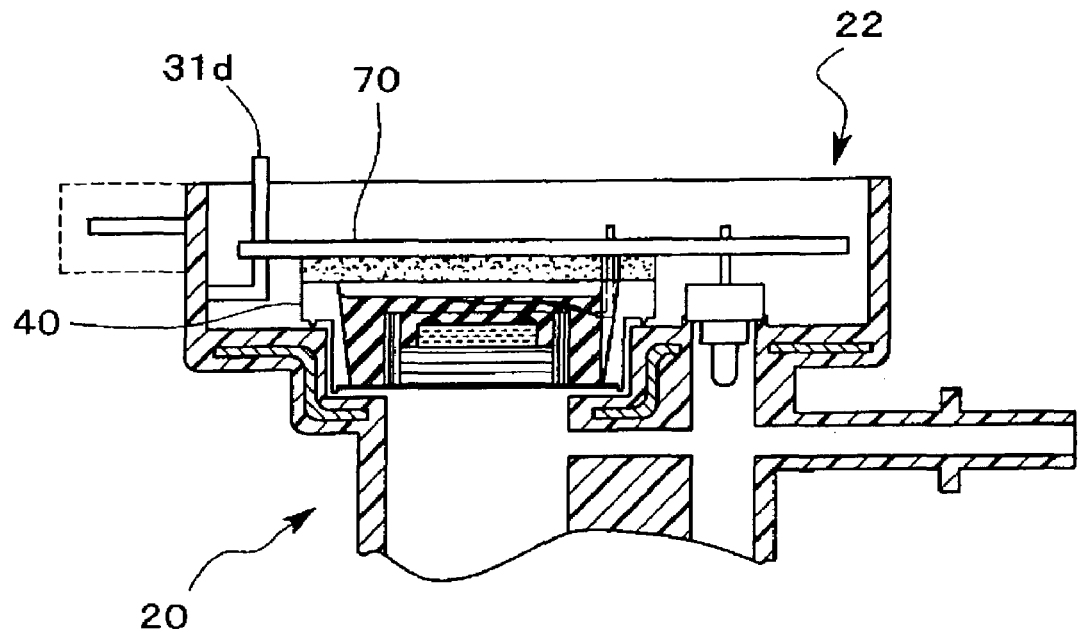
FIGS. 15(A) and (B) are explanatory views showing the manner of attachment of the electronic circuit board 70 and a casing 80.
Figure 15:
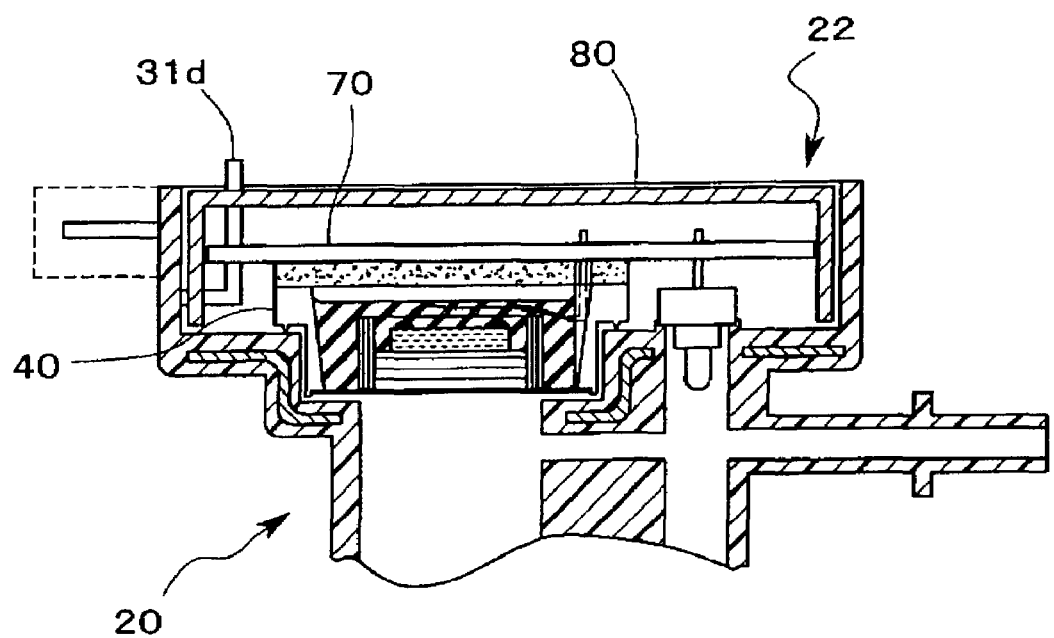

Next, as shown in FIG. 15(B), the casing 80 is attached to the housing portion 22 (step S270). At this time, the terminal 31d of the connector 31 is inserted through the connection hole 85 formed in the casing 80 and then soldered or brazed to the casing 80. Thus is completed the attachment of the casing 80. Subsequently, a resin (urethane resin in the present embodiment) is filled into the interior of the housing portion 22 (step S280) so as to embed the detecting-element assembly 40 and the electronic circuit board 70 in urethane resin through molding. FIG. 15 does not show the resin used in molding. Subsequently, a gas which contains gasoline vapor and whose gasoline vapor concentration has already been measured by use of another detecting apparatus is introduced into the measuring chamber 28. The gas sensor 10 is activated, and an output from the gas sensor 10 is calibrated (step S290). According to the present embodiment, the gas sensor 10 is calibrated in the following manner: on the basis of the results of detection, a calibration curve showing the relationship between an output from the gas sensor 10 and gasoline concentration obtained through measurement by another measuring apparatus is obtained and written onto an EEPROM contained in the microprocessor 91. Alternatively, before urethane resin is filled, a trimmer or the like provided on the electronic circuit board 70 may be adjusted for calibration. In the latter case, preferably, an opening for allowing an adjustment tool to be inserted therethrough is formed in the casing 80, and adjustment is performed after the casing 80 is attached in place (before molding with resin is performed).

The above-described method for manufacturing a gas sensor can easily manufacture a sensor configured such that the detecting-element assembly 40 is joined to a bottom part of the housing portion 22 by use of the flange portion 41 to thereby provide a sufficiently long path between the joint of the flange portion 41 and the piezoelectric element 51 housed in the detecting-element assembly 40. Also, since an average clearance of 1 millimeter or greater can be formed along the outer circumferential surface of the detecting-element assembly 40, a sensor unsusceptible to collection of foreign matter or the like can be easily manufactured. As a result, sufficient reliability and durability can be imparted to a sensor which is to be used in the market over a long term.

Figure 16:
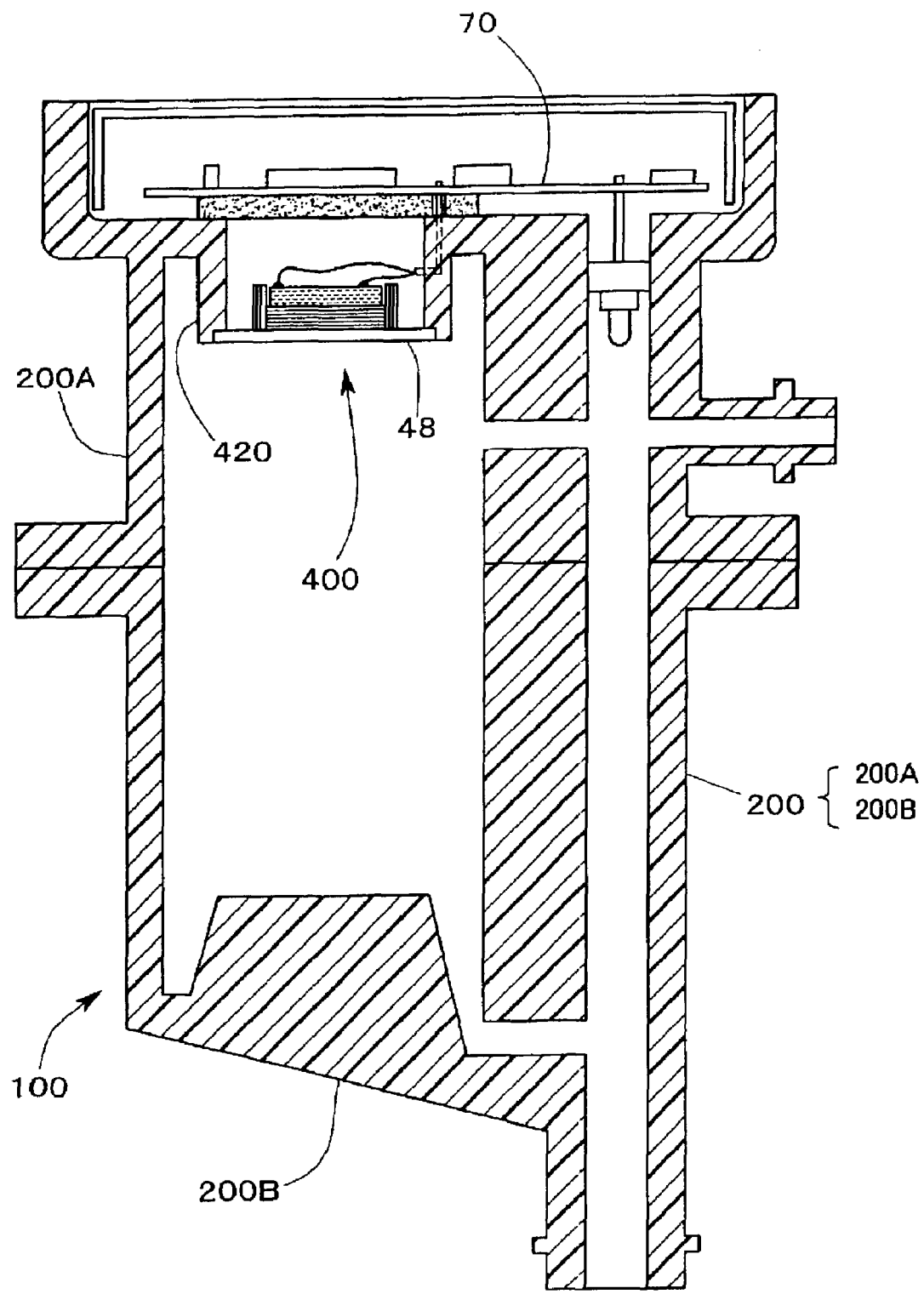
FIG. 16 is a sectional view showing the configuration of a gas sensor according to a second embodiment of the present invention.

(H) Second Embodiment:

Next, a second embodiment of the present invention will be described. FIG. 16 is a sectional view showing a schematic configuration of a sensor 100 according to the second embodiment. The second embodiment is similar to the first embodiment except that a detecting-element assembly 400 is formed integrally with a flow path formation member 200. As shown in FIG. 16, the flow path formation member 200 is divided into two members, or an upper member and a lower member, at substantially the longitudinal center of a measuring chamber 28. The upper member having the housing portion 22 formed thereon is called an upper flow path member 200A, and the lower member having a reflective portion 30 formed therein is called a lower flow path member 200B. The shape of an assembly of the upper and lower flow path members 200A and 200B is similar to that of the first embodiment except that the detecting-element assembly 400 is formed integrally with the flow path formation member 200A. In this sensor 100, a container portion 420 of the detecting-element assembly 400 is formed from resin integrally with the housing portion 22 of the flow path formation member 200A. This container portion 420 assumes a shape corresponding to the shape of an assembly of the flange portion 41 and the casing body portion 43 of the first embodiment, and is open-ended.

Figure 12:
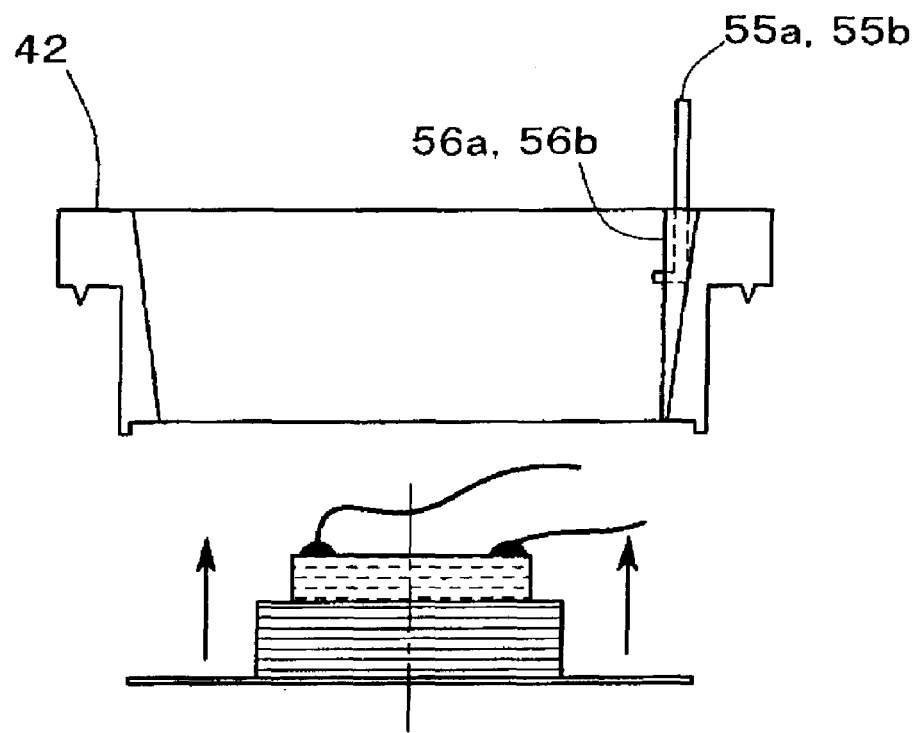
FIGS. 12(A) and (B) are explanatory views showing a procedure for attaching the piezoelectric element assembly to the element casing 42.
Figure 12:
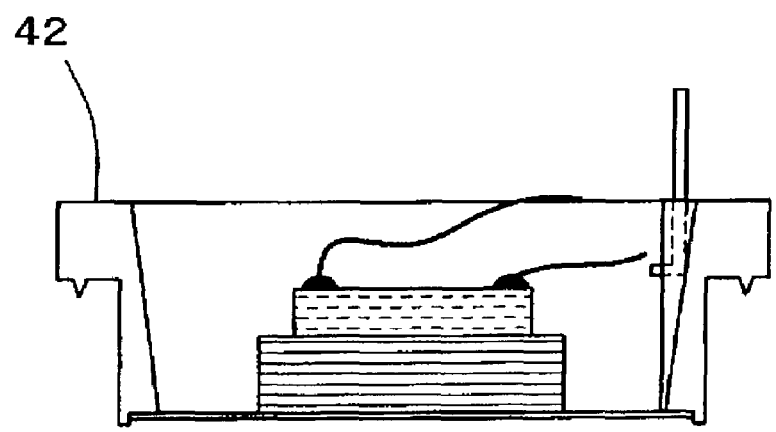
Figure 13:
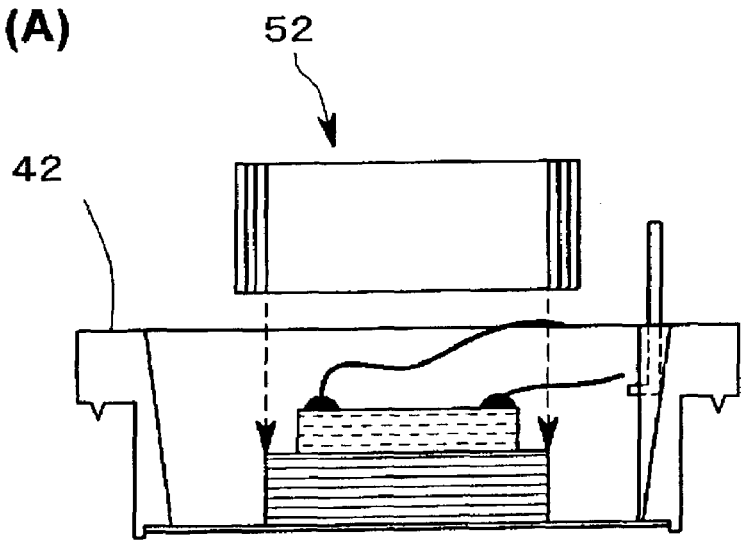
FIGS. 13(A), (B) and (C) are explanatory views showing a procedure for manufacturing the detecting-element assembly 40.
Figure 13:
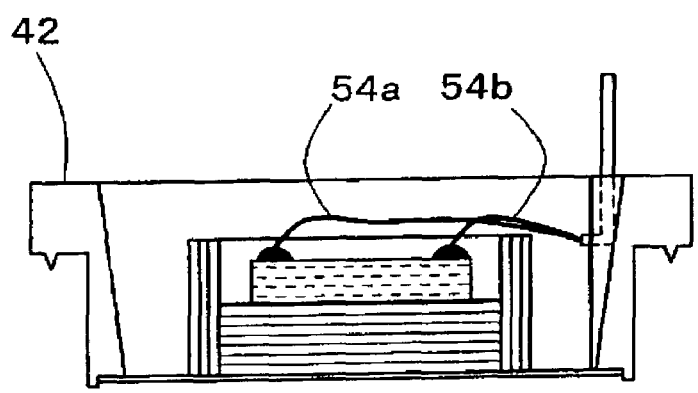
Figure 13:
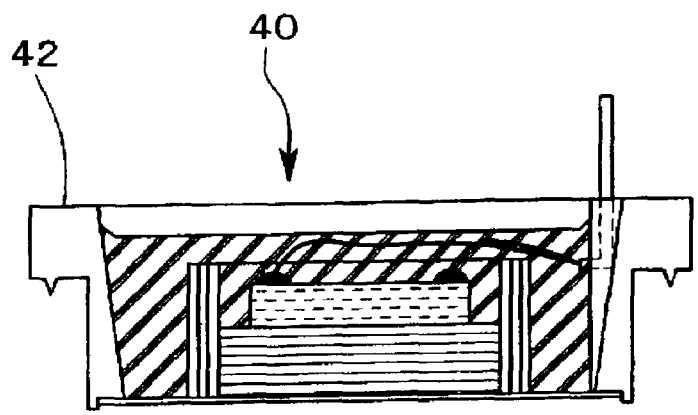

Before the upper flow path member 200A and the lower flow path member 200B are assembled together, the protective film 48 on which the acoustic matching plate 50 and the piezoelectric element 51 are mounted is attached to the open end of the container portion 420 of the upper flow path member 200A such that a peripheral portion of the protective film 48 is bonded to the open end of the container portion 420 by use of an adhesive in a manner similar to that shown in FIG. 12. Subsequently, as shown in FIG. 13, the attachment of the tubular member 52, the connection of the lead wires 54a and 54b, and the filling of urethane resin are performed. Furthermore, the disposition of the cushioning material 88, the attachment of the electronic circuit board 70, and the filling of a synthetic resin are performed. At the earliest after urethane resin is filled into the container portion 420, the upper flow path member 200A and the lower flow path member 200B are assembled together. As a result, as shown in FIG. 16, the thus-obtained sensor 100 exhibits functions and the like similar to those as exhibited by the first embodiment.

According to the above-described configuration, the detecting-element assembly 400 which houses the piezoelectric element 51, and the housing portion 22 of the upper flow path member 200A are formed integrally with each other; i.e., no joint is involved. Therefore, the phenomenon that ultrasonic waves, which leak into the interior of the detecting-element assembly 400 from the piezoelectric element 51, reflectively return from a joint is not involved. Reflected waves which could return are from the joint between the upper flow path member 200A and the lower flow path member 200B. However, since the path extending from the joint is very long, the reflected waves are sufficiently damped, whereby the influence of the reflected waves in the form of, for example, reverberations is sufficiently reduced.

Also, in the second embodiment shown in FIG. 16, a sufficient clearance is formed along the outer circumferential surface of the container portion of the detecting-element assembly 400. In distinction to the first embodiment, the second embodiment does not involve concentric alignment between the detecting-element assembly 400 and the recess. Therefore, manufacturing does not involve variations in clearance among products, and a problem of collection of foreign matter in the clearance is sufficiently suppressed. Furthermore, manufacturing does not involve ultrasonic welding, and sealing in relation to the measuring chamber 28 can be sufficiently established.

While the present invention has been described with reference to the embodiments, the present invention is not limited thereto. Without departing from the scope of the invention, as defined by the claims appended hereto, the present invention is applicable to, for example, temperature and specific heat sensors which utilize ultrasonic waves and to sensors which detect various properties of gas by use of techniques other than an ultrasonic technique.

This application is based on Japanese Patent Application No. 2002-107459 filed Apr. 10, 2002, incorporated herein by reference in its entirety.

What is claimed is:

1. A sensor comprising: an element for transmitting and receiving ultrasonic waves and electric signals; an element casing housing the element; a measuring chamber; and a housing portion located above the measuring chamber, the element casing being attached to the housing portion, and an inlet for introducing an object to be measured by use of ultrasonic waves into the measuring chamber, wherein the element casing comprises (i) a body portion for housing the element at a first end thereof, and (ii) a flange portion provided at a second opposite end of the element casing;

the element casing and element are housed in the housing portion;

the element casing is attached to an inner wall of the housing portion via the flange portion;

the element is attached to a first end of the body portion;

the body portion is tubular, and the first end of the body portion is sealed with a sealing member;

the element is bonded to the sealing member directly or via a member aiding transmission of ultrasonic waves; and the tubular body portion is filled with resin while housing the element.

2. The sensor as described in claim 1, wherein the body portion is molded from a synthetic resin.

3. The sensor as described in claim 1, wherein an inside diameter of the portion of the housing portion to which the element casing is attached is greater than an outside diameter of the body portion.

4. The sensor as described in claim 3, wherein an inside diameter of the portion of the housing portion to which the element casing is attached is at least 2 mm greater than an outside diameter of the body portion.

5. The sensor as described in claim 1, wherein the object to be measured is gas; and the sensor further comprises a detecting portion for detecting a condition of transmission of ultrasonic waves by means of an electric signal received from the element and determining a concentration of the gas from the detected condition.

6. The sensor as described in claim 5, wherein the element casing is provided at a first end of the measuring chamber, and a reflective portion for reflecting ultrasonic waves is provided at a second end of the measuring chamber; and the detecting portion is means for measuring time between transmission of an ultrasonic wave from the element casing and reception of the ultrasonic wave reflected from the reflective portion and determining the concentration of the gas from the measured time.

7. The sensor as described in claim 1, wherein an outside diameter of the flange portion is greater than that of the body portion.

8. The sensor as described in claim 1, wherein the element casing has a protrusion formed on a lower surface of the flange portion which joins the flange portion to the housing portion.

9. The sensor as described in claim 1, wherein the element casing has an inside wall which slopes inwardly toward the first end of the element casing.

10. The sensor as described in claim 1, wherein the flange portion protrudes outwardly from the body portion of the element casing.

11. The sensor as described in claim 1, wherein the element casing has an inner diameter that is smaller at the first end than at the second opposite end.

12. The sensor as described in claim 1, wherein the element casing integrally comprises said body portion and said flange portion as a single unit.

13. A method for manufacturing a sensor comprising: an element for transmitting and receiving ultrasonic waves and electric signals; an element casing housing the element; a measuring chamber; and a housing portion located above the measuring chamber, the element casing being attached to the housing portion, and an inlet for introducing an object to be measured by use of ultrasonic waves into the measuring chamber, wherein the element casing comprises (i) a body portion for housing the element at a first end thereof, and (ii) a flange portion provided at a second opposite end of the element casing;

the element casing and element are housed in the housing portion;

the element casing is attached to an inner wall of the housing portion via the flange portion;

the element is attached to a first end of the body portion;

the body portion is tubular, and the first end of the body portion is sealed with a sealing member;

the element is bonded to the sealing member directly or via a member aiding transmission of ultrasonic waves;

and the tubular body portion is filled with resin while housing the element, the method comprising the steps of:

forming the element casing from resin in such a manner that the element casing has a body portion for housing the element, and a flange portion integrated with the body portion;

housing the element in the body portion at an end of the body portion and then substantially filling the interior of the body portion with resin; and fixing the element casing in such an orientation that the body portion is located within the measuring chamber and such that the flange portion is attached to the housing portion.

* * * * *